United States Patent
Onikienko et al.

(10) Patent No.: US 10,052,376 B2
(45) Date of Patent: Aug. 21, 2018

(54) LASER-BASED VACCINE ADJUVANTS

(71) Applicants: Sergey B. Onikienko, St-Petersburg (RU); Alexander V. Zemlyanoi, St-Petersburg (RU); Boris A. Margulis, St-Petersburg (RU); Irina V. Guzhova, St-Petersburg (RU); Anna A. Pimenova, St-Petersburg (RU)

(72) Inventors: Sergey B. Onikienko, St-Petersburg (RU); Alexander V. Zemlyanoi, St-Petersburg (RU); Boris A. Margulis, St-Petersburg (RU); Irina V. Guzhova, St-Petersburg (RU); Anna A. Pimenova, St-Petersburg (RU)

(73) Assignee: ALTERNATIVE INNOVATIVE TECHNOLOGIES LLC, West Roxbury, MA (US)

( * ) Notice: Subject to any disclaimer, the term of this patent is extended or adjusted under 35 U.S.C. 154(b) by 85 days.

(21) Appl. No.: 14/255,931

(22) Filed: Apr. 17, 2014

(65) Prior Publication Data
US 2014/0335110 A1   Nov. 13, 2014

Related U.S. Application Data

(63) Continuation of application No. 13/428,275, filed on Mar. 23, 2012, which is a continuation of application No. 12/754,081, filed on Apr. 5, 2010, which is a continuation of application No. PCT/IB2008/002637, filed on Oct. 6, 2008.

(51) Int. Cl.
| | |
|---|---|
| *A61K 39/12* | (2006.01) |
| *A61N 5/06* | (2006.01) |
| *A61N 5/067* | (2006.01) |
| *C12N 15/90* | (2006.01) |
| *A61K 39/29* | (2006.01) |
| *A61K 39/095* | (2006.01) |
| *A61K 39/145* | (2006.01) |
| *A61K 39/39* | (2006.01) |
| *C12N 7/00* | (2006.01) |
| *A61K 39/00* | (2006.01) |

(52) U.S. Cl.
CPC ............ *A61K 39/29* (2013.01); *A61K 39/095* (2013.01); *A61K 39/12* (2013.01); *A61K 39/145* (2013.01); *A61K 39/292* (2013.01); *A61K 39/39* (2013.01); *A61N 5/0613* (2013.01); *C12N 7/00* (2013.01); *A61K 2039/53* (2013.01); *A61K 2039/545* (2013.01); *A61K 2039/55516* (2013.01); *A61N 2005/067* (2013.01); *A61N 2005/0659* (2013.01); *A61N 2005/0662* (2013.01); *C12N 2730/10134* (2013.01); *C12N 2750/00034* (2013.01); *C12N 2760/16034* (2013.01); *C12N 2760/16134* (2013.01)

(58) Field of Classification Search
None
See application file for complete search history.

(56) References Cited

U.S. PATENT DOCUMENTS

| | | | | |
|---|---|---|---|---|
| 2005/0281783 A1* | 12/2005 | Kinch | ................ | A61K 39/0011 424/93.2 |
| 2006/0241577 A1* | 10/2006 | Balbierz | ............ | A61B 18/1206 606/32 |

FOREIGN PATENT DOCUMENTS

RU   2345788 C2 *   2/2009   ........... A61N 5/0613

OTHER PUBLICATIONS

Zhang et al. "Vaccination with a DNA vaccine based on human PSCA and HSP70 adjuvant enhances the antigen-specific CD8+ T-cell response and inhibits the PSCA+ tumors growth in mice" J Gene Med 2007, 9, 715-726.*
Kashiwagi et al. "Laser vaccine adjuvants History, progress, and potential" Human Vaccines & Immunotherapeutics, 10(7) pp. 1892-1907, 2014.*

* cited by examiner

*Primary Examiner* — Daniel E Kolker
*Assistant Examiner* — James Rogers
(74) *Attorney, Agent, or Firm* — JWIP & Patent Services, LLC; Jacob G. Weintraub, Esq.

(57) ABSTRACT

The invention is directed to a vaccine for generating an enhanced immune response in a subject previously exposed to non-destructive laser radiation, as compared to an immune response in a subject previously non-exposed to non-destructive laser radiation. The invention is also directed to use of a composition comprising a vaccine for use in combination with non-destructive laser radiation for generating an enhanced immune response from a subject, as compared to an immune response without the use of laser radiation. The laser exposure acts as an adjuvant for the vaccine, increasing the efficacy and/or potency of the vaccine.

9 Claims, 4 Drawing Sheets

LASER-BASED VACCINE ADJUVANTS

RELATED APPLICATIONS

This application is a Continuation of U.S. application Ser. No. 13/428,275, filed Mar. 23, 2012, which in turn is a Continuation of U.S. application Ser. No. 12/754,081, filed Apr. 5, 2010, which in turn is a Continuation of International Application No. PCT/IB2008/002637 filed on Oct. 6, 2008, which claims priority to Russian Patent Applications RU 2007113393, filed 4 Oct. 2007, and RU 2008121934, filed 27 May 2008, all of which are incorporated herein by reference in their entirety.

BACKGROUND OF THE INVENTION

As the use of killed whole or attenuated live vaccines of the previous century gives way to the use of more sophisticated subunit protein and DNA vaccines that will characterize vaccines in next several decades, finding safe and effective vaccine adjuvants is becoming increasingly important. Although the new generations of vaccines are more targeted by design, they are also far less immunogenic and typically require powerful adjuvants to induce sufficient immune responses in the human body. It has also been challenging to develop adjuvants with sufficient efficacy and safety to satisfy the stringent requirements of Western regulatory agencies.

The pace of vaccine adjuvant development has been slower in comparison to the rapid advance of vaccine development. Currently, very few chemical or biological adjuvants are approved for human use in the West. Aluminum salts (aluminum hydroxide, aluminum phosphate or alum) have been used in vaccine preparations for over 80 years (Glenny et al. 1926). They have the ability to create more antigenic precipitates with some vaccines, enhance the uptake by antigen-presenting cells by increasing the local concentration of antigen at the injection site, and stimulate immunogenicity by direct or indirect stimulation of dendritic cells, activation of complement, and by inducing the release of chemokines (Hogen Esch 2002). While these mechanisms can be relevant in stimulating type II (antibody-mediated) immune responses, they do not induce cytotoxic T-cell or cell-mediated immune responses. Aluminum salts also cause side effects in a certain percentage of the population that receives such vaccinations.

Recently, several additional adjuvants received regulatory approval in Europe. Monophosphoryl lipid A (MPL), a derivative of the lipopolysaccharides of the bacterial cell wall, was recently approved by the European Medicines Agency (EMEA) in the vaccine FENDRIX® (GlaxoSmithKline), a vaccine against hepatitis B. MPL, developed by Corixa (Seattle, Wash.), is an adjuvant in several other vaccines that are currently in clinical testing. The EMEA also recently approved the oil-in-water emulsion adjuvant MF59 for use with FOCETRIA®, a Novartis' pandemic influenza vaccine. Neither of these has received market approval by the FDA.

There are a wide number of substances that could potentially be used as adjuvants: haptens, hemocyanin, oil-in-water emulsions, surfactants, bacterial and viral components, HLA molecules, cytokines, toll receptor agonists, and heat shock proteins. Many of these are powerful immunostimulators that induce both type I and type II immune responses. However, most of these also have a high potential for side effects and have therefore not been approved for human use. Both the FDA and the EMEA have adopted requirements for vaccine adjuvants that are strict and have grown increasingly stringent in recent years. Fundamentally, this orientation is based on the fact that vaccines are used to prevent illness, not treat disease. The safety of a vaccine must be weighed against a hypothetical health threat, in comparison to therapies whose safety profiles are measured against the actual disease they are designed to treat. The result is that the presumption of safety is already far higher for vaccines.

SUMMARY OF THE INVENTION

The present invention is directed to a vaccine for generating an enhanced immune response in a subject previously exposed to non-destructive laser radiation, as compared to an immune response in a subject previously non-exposed to the non-destructive laser radiation. Such vaccine turns out to have efficacy in the subjects who are immunocompromised or non-responsive to the vaccine without the previous exposure to the laser radiation. It is contemplated that the vaccine of the present invention can comprise an amount of HSP 70 for generating an enhanced immune response. The vaccine of the present invention generates the enhanced response from the subject with increased HSP 70 concentration due to the previous exposure to laser radiation. Also, according to the invention, the vaccine generates the enhanced response the subject with an increased Langerhans cell concentration due to the previous exposure to laser radiation. The referenced enhanced immune response comprises an increase in an antibody titer specific to the vaccine. Another kind of an enhanced immune response generated by the vaccine is an increased resistance to a condition, which for, example, can be a decrease in an infection rate upon exposure to a pathogen specific to the vaccine, or it can be a decrease in mortality in response to an exposure to the pathogen specific to the vaccine.

The present invention is also directed to the use of a composition comprising a vaccine for use in combination with laser radiation for generating an enhanced immune response from a subject, as compared to an immune response without the use of laser radiation. The composition can further comprise an amount of HSP 70. The referenced enhanced immune response can be generated by the vaccine in a subject who is immunocompromised or who is non-responsive to the vaccine without the previous exposure to laser radiation.

The invention contemplates methods of administering a vaccine to a subject including exposing an area of an epidermal layer of skin of the subject to a laser wherein laser exposure does not cause significant or irreversible damage cells in the exposed area, and contacting the subject with the antigen at the site of laser exposure, thereby administering the vaccine. Irreversible damage to the cells includes cell death, either upon exposure to the laser, or as a direct result of laser exposure. Significant damage is damage to at least 1%, 0.5%, 0.25%, 0.1%, 0.01%, or 0.001% of cells exposed to the laser.

The invention further provides methods to increase HSP 70 concentration and/or Langerhans cell concentration at or near the site of laser exposure as compared to a site not exposed to laser by exposing an epidermal layer of the skin to laser wherein laser exposure does not cause significant or irreversible damage cells in the exposed area.

In the methods of the invention, the frequency of the laser is about 1 to about 20 kilohertz, the power of the laser is about 0.5 to about 10 watts, about 1 watt to 8 watts, about 1 watt to about 5 watts, about 1 watt to about 3 watts, or about 1.5 watts and the pulse duration is about 1 to about 1000 nanoseconds, about 1 to 500 nanoseconds, about 1 to 100 nanoseconds, about 1 to 50 nanoseconds, about 5 to 20 nanoseconds, or about 10 nanoseconds.

In the methods of the invention, the laser exposure takes place as close as possible to the time of the vaccine, either before or after administration of the vaccine, to within about an hour, within about 45 minutes, within about 30 minutes, within about 15 minutes, to within about 10 minutes of vaccine administration.

The methods of the invention include administering a vaccine to a laser exposed area of an epidermal layer of skin of the subject to provide an increase in a detectable response to the vaccine as compared to administering a vaccine to an epidermal layer of skin area of a subject not exposed to laser. In the methods of the invention, an increase in a detectable response can include an increase in antibody titer specific to the vaccine, an increase in resistance to a condition as demonstrated, for example by a decrease in infection rate upon exposure to a pathogen specific to the vaccine, a decrease in mortality in response to exposure to a pathogen specific to the vaccine, and/or a decrease in time to detect a response to the vaccine.

The methods of the invention can further include detecting a response to the vaccine. In other embodiments, the invention can also include identifying a subject in need of vaccination. In some embodiments of the invention, the subject is immunocompromised. In some embodiments, the invention further includes co-administration of the vaccine with heat shock protein 70.

The invention provides methods that can be practiced using any laser that provides a wavelength that can stimulate an immune response to an antigen (see, e.g., Table 2). Lasers for use in the methods of the invention include, but are not limited to a copper bromide laser and a neodymium-doped yttrium aluminium garnet; (Nd:YAG) laser. Laser wavelengths for use in the methods of the invention include, but are not limited to 510 nm and 578 nm. Laser beam sizes for use in the method of the invention include, but are not limited to 1-10 mm, 2-8 mm, 2-7 mm, or 3-5 mm.

The invention provides methods for contacting a subject with a vaccine at a site of laser exposure by injection. The invention provides methods for injection including, but not limited to intradermal, subcutaneous, and intramuscular injection.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings.

DETAILED DESCRIPTION OF THE PREFERRED EMBODIMENTS

Definitions

Figure 1:
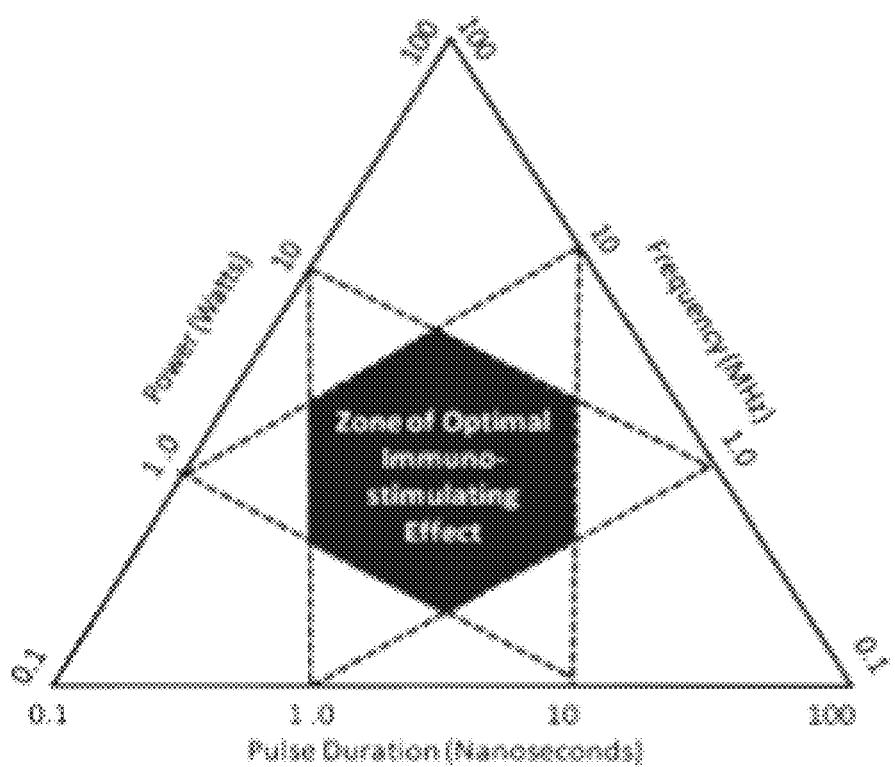
FIG. 1 shows a schematic of the optimal conditions for the laser-based immune enhancement methods of the invention of the skin at a specific wavelength of irradiation.

As used herein "treating" a disease in a subject or "treating" a subject having a disease refers to subjecting the subject to a pharmaceutical treatment, e.g., the administration of a drug, such that the extent of the disease is decreased or prevented. For example, treating results in the reduction of at least on sign or symptom of the disease or condition. Treatment includes (but is not limited to) administration of a composition, such as a pharmaceutical composition, in combination with exposure to a laser as described herein, and may be performed either prophylactically or subsequent to the initiation of a pathologic event. Treatment can require administration of an agent and/or treatment more than once.

As used herein, "preventing" as it refers to a condition means that a subject in which the occurrence of a condition is prevented, will show no detectable symptoms of a condition of interest. No detectable symptoms means less than 10%, 5%, 1.0%, 0.5%, 0.1% or 0.01% of the level of detectable symptoms of a subject that has been diagnosed with a condition of interest.

As used herein, a "condition" includes any abnormality that can occur in a subject including any disease, infection, disorder, tumor, cancer, inflammatory condition, or cellular structure associated with disordered function.

To "prevent the occurrence of a condition" also means to stop or delay the occurrence of a condition of interest. Prevention can require administration of an agent and/or treatment more than once.

As used herein, "significant and irreversible damage" is understood as causing harm to the cells which directly leads to death of the cells exposed to the laser in the methods of the invention. Irreversible damage to a cell means that the function of the cell is negatively altered or compromised and cannot return to normal. Irreversible damage can occur when the cell is destroyed, physically removed from its environment, or when the function of the cell is compromised, for example by irreversible disruption of the membrane or destruction or damage to one or more of the organelles or processes within the cell. Significant damage refers to the number of cells that are killed, i.e., irreversibly damaged, either as a ratio (percent) of the cells exposed to the laser, as a defined number of cells per laser exposure, or a defined area of cells. Significant damage is damage to at least 1%. 0.5%, 0.25%. 0.1%, 0.001%, or 0.0001% of the cells expose to the laser.

As used herein, "adjuvant" is understood as an aid or contributor to increase the efficacy or potency of a vaccine or in the prevention, amelioration, or cure of disease by increasing the efficacy or potency of a therapeutic agent as compared to a vaccine or agent administered without the adjuvant. An increase in the efficacy or potency can include a decrease in the amount of vaccine or agent to be administered, a decrease in the frequency and/or number of doses to be administered, or a more rapid or robust response to the agent or vaccine (i.e., higher antibody titer). An adjuvant can be an agent or laser.

As used herein, "subject" refers to a mammal. A human subject can be known as a patient.

As used herein, "mammal" refers to any mammal including but not limited to human, mouse, rat, sheep, monkey, goat, rabbit, hamster, horse, cow or pig.

A "non-human mammal", as used herein, refers to any mammal that is not a human.

As used herein "exposing" means treating with a laser for an exposure time useful to the invention. In one embodiment, exposing means to expose a subject to a laser applied in a pulse, wherein the pulse is applied for a particular duration. The range of pulse durations are in the hundreds of picoseconds to tens of nanoseconds (for example, about 100, 200, 300, 400, 500, 600, 700, 800, 900 picoseconds, or about 1, 2, 3, 4, 5, 6, 7, 8, 9, 10, 12, 15, 20, 25, 30, 35, 40, 45, 50, 75, or 100 nanoseconds). It is understood that the actual pulse length will vary somewhat based on the limitations of the laser and the switching rate/shutter speed. In another embodiment, "exposing" means to expose a subject to a laser of a particular pulse frequency. Optimal frequencies range from about 1 kHz to about 20 kHz (for example, 1, 5, 10, 15, 20 kHz), with typical pulse frequencies in the 5, 6, 7, 8, 9, or 10 kHz frequency. It is understood that the actual frequency will vary somewhat based on the limitations of the laser and the switching rate/shutter speed. In another embodiment, "exposing" means to expose a subject to a laser of a particular wavelength where the range of wavelengths can range from the visible light to the near infrared portion of the electromagnetic spectrum (approximately 400 nm to 1400 nm, for example, 400, 425, 450, 475, 500, 525, 550, 575, 600, 625, 650, 675, 700, 725, 750, 775, 800, 825, 850, 875, 900, 925, 950, 975, 1000, 1125, 1150, 1175, 1200, 1225, 1250, 1275, 1300, 1325, 1350, 1375, and 1400 nm), and are typically about 500-1100 nm. In another embodiment, "exposing" means to expose a subject to a laser with a particular peak power, where the range of power is 0.1 to 10 Kwatts (for example, about 0.1, 0.2, 0.3, 0.4, 0.5, 0.6, 0.7, 0.8, 0.9, 1, 2, 3, 4, 5, 6, 7, 8, 9, and 10 Kwatts) and are typically about 1-5 Kwatts. In another embodiment, "expose" means to expose a subject to a laser for a particular length of time. The range of exposures can be about 5 seconds to about 600 seconds (for example, about 5, 10, 20, 30, 40, 50, 60, 70, 80, 90, 100, 150, 200, 250, 300, 350, 400, 450, 500, 550, 600 seconds). In another embodiment, "expose" means to expose a particular area of the subject. Typical exposure areas are about 1-100 mm$^2$ (for example, 1, 2, 3, 4, 5, 6, 7, 8, 9, 10, 20, 30, 40, 50, 60, 70, 80, 90 and 100 mm$^2$).

In one embodiment, the exposure to a laser occurs prior to administration of said agent. The exposure to said laser occurs about 1, 2, 3, 4, 5, 6, 7, 8, 9, 10, 20, 30, 40, 50 seconds, about 1, 2, 3, 4, 5, 10, 15, 20, 25, 30, 35, 40, 45, 50, 55 minutes or about 1, 2, 3, 4, 5, 6, 7, 8, 9, 10 or more hours before administration of said agent.

In another embodiment, the exposure to said laser occurs about 1, 2, 3, 4, 5, 6, 7, 8, 9, 10, 20, 30, 40, 50 seconds, about 1, 2, 3, 4, 5, 10, 15, 20, 25, 30, 35, 40, 45, 50, 55 minutes or about 1, 2, 3, 4, 5, 6, 7, 8, 9, 10 or more hours after administration of said agent.

As used herein, a "laser" refers to an electronic-optical device that emits coherent light radiation. A typical laser emits light in a narrow, low-divergence monochromatic (single-colored, if the laser is operating in the visible spectrum), beam with a well-defined wavelength. In this respect, laser light is in sharp contrast with such light sources as the incandescent light bulb, which emits light over a wide area and over a wide spectrum of wavelengths.

As used herein, a "laser" includes any laser that is currently available or may become available that can provide the appropriate pulse duration, power, and pulse frequency required by the methods of the instant invention. Currently available lasers that can be used in the methods of the invention include, but are not limited to, a copper bromide laser such as the Norseld DualYellow copper bromide laser (511 and 578 nm) or the Asclepion ProYellow+ copper (511 and 578 nm), or a neodymium-doped yttrium aluminium garnet (Nd:YAG) lasers such as a Q-switched Yag laser such as the RMI 15 Q-Switched Diode-Pumped Solid State Laser with an output at either 532 nm or 1064 nm.

As used herein, "administering" refers to any method according to the invention including but not limited to injection, subcutaneous, transcutaneous, intramuscular, intraperitoneal, intracranial and spinal injection, administration directly to a blood vessel, including artery, vein or capillary, intravenous drip, ingestion via the oral route, inhalation, transepithelial diffusion (such as via a drug-impregnated, adhesive patch) or by the use of an implantable, time-release drug delivery device, which may comprise a reservoir of exogenously-produced agent or may, instead, comprise cells that produce and secrete the therapeutic agent or topical application. Additional methods of administration are provided herein below in the section entitled "Dosage and Administration." As used herein, "administering" can also refer to exposure of a subject to a laser, preferably for a therapeutic use.

As used herein, "contacting" means exposing a subject to, for example by any of the methods of administration described herein. "Contacting" refers to exposing a subject to, for example, an agent for a duration of about 1, 5, 10, 20, 30, 40, 50 minutes, about 1, 2, 5, 10, 20, 24 hours, about 2, 3, 4, 5, 6, 7, 8, 9, 10 days or more. In one embodiment, "contacting" refers to exposing a subject more than once, for example about 2, 3, 4, 5, 6, 7, 8, 9, 10 times or more.

As used herein, an "agent" refers to any protein, recombinant protein, small molecule, DNA, RNA, antigen, parasite, virus, bacteria, or other prokaryotic or eukaryotic cells, either whole cells or fragments thereof, or combination thereof.

An "agent" also includes a vaccine. A used herein, a "vaccine" is a preparation which is used to increase immunity of a subject to a particular condition or antigen.

An "antigen" is understood as any compound that can be used to stimulate a specific immune response. An antigen can be an isolated or purified protein, nucleic acid, carbohydrate, small molecule, and the like. Alternatively, an antigen can be a complex mixture, naturally or artificially generated including a mixture of one or more of protein, nucleic acid, carbohydrate, small molecule optionally in the form of a pathogen, particularly a killed or attenuated pathogen. Antigens include self- and non-self antigens. For example, an antigen can be a protein that is not normally present in a subject, e.g., a cancer cell. An antigen can also be a contraceptive protein (e.g., riboflavin carrier protein).

A "nucleic acid therapeutic" or "nucleic acid antagonist" can be any nucleic acid (DNA, RNA, or a combination thereof) or an analog thereof (e.g., PNA) optionally including one or more modifications (see, e.g., U.S. Pat. Nos. 7,015,315 and 6,670,461, incorporated herein by reference) to modulate pharmacokinetic or pharmacodynamic properties of the nucleic acid. Nucleic acid antagonists can be antisense oligonucleotides (see, e.g., U.S. Pat. No. 5,366, 878; or 6,921,812, both incorporated herein by reference), small interfering (si)RNA (see, e.g., U.S. Pat. No. 7,056,704, incorporated herein by reference), short hairpin RNA (see, e.g., US Patent publication 20080119427, incorporated herein by reference), or other double stranded RNA molecules (see, e.g., US Patent publication 20070265220, incorporated herein by reference). Nucleic acid antagonists are well known in the art.

A "small molecule" is understood as is meant a compound having a molecular weight of no more than about 1500 daltons, 1000 daltons, 750 daltons, 500 daltons. A small molecule is not a nucleic acid or polypeptide.

By "analog" is meant a molecule that is not identical, but has analogous functional or structural features.

As used herein, "increase" as it refers to a response means elevating the level of response (for example, cell membrane permeability, production or secretion of Heat Shock Proteins (HSPs), increased concentration, maturation and/or activation of Langerhans cells at the site of laser exposure) following administration of an agent or antigen by at least about 2-fold (for example about 2, 3, 4, 5, 10, 15, 20, 25, 30, 35, 40, 45, 50, 55, 60, 65, 70, 75, 80, 85, 90, 95, 100, 1000-fold or more) or at least about 2% (for example, about 2, 3, 4, 5, 10, 15, 20, 25, 30, 35, 40, 45, 50, 55, 60, 65, 70, 75, 80, 85, 90, 95, 99, or 100%), in a subject that has been exposed to a laser, as compared to an untreated subject.

As used herein, a "heat shock protein" refers to a group of proteins whose expression is increased when cells are exposed to elevated temperatures or other stress. The HSPs are named according to their molecular weights. For example, Hsp60, Hsp70 and Hsp90 (the most widely-studied HSPs) refer to families of heat shock proteins on the order of 60, 70 and 90 kilodaltons in size, respectively. The small 8 kilodalton protein ubiquitin, which marks proteins for degradation, also has features of a heat shock protein.

As used herein, a "detectable response" includes a discernable, preferably a measurable level of a response that occurs in a subject that has been exposed to a laser, as described herein, but not in a subject that has not been exposed to a laser. A "response" that is detected includes, but is not limited to, one or more of an increase in immunogenicity, an increase in an immune response, an increase in the concentration of Langerhans cells at the site of irradiation, an increase in the maturation or activation of Langerhans cells, an increase in the number of mature Langerhans cells, an increase in the production of Heat Shock Proteins (HSPs), an increase in the secretion of HSPs, an increase in cell membrane permeability, an increase in the level of one or more cytokine or chemokine, an increase in antibody titer to an agent of interest, an increase in lymphocyte cytotoxic activity, an increase in response to antigen challenge, or an increase in viability in response to pathogen challenge.

A "detectable response" means a response that is at least about 0.01%, 0.5%, 1%, 10%, 20%, 30% or more than the response of a subject that has not been exposed to a laser. A "detectable response" also means a response that is at least about 0.5, 1, 2, 3, 4, 5, 10, 20, 30, 40, 50, 60, 70, 80, 90, 100, 1000-fold or more greater than the response of a subject that has not been exposed to a laser.

As used herein, "detecting a response" means performing an assay to determine if a response has occurred. In an embodiment, the response can be zero or below the limit of detection of the assay method.

As used herein, "immunogenicity" refers to the ability, for example the ability of an agent, to induce humoral and/or cell-mediated immune responses in a subject.

As used herein, "immune response" refers to a response made by the immune system of an organism to a substance, which includes but is not limited to foreign or self proteins. There are three general types of "immune response" including, but not limited to mucosal, humoral, and cellular "immune responses."

A "mucosal immune response" results from the production of secretory IgA (sIgA) antibodies in secretions that bathe all mucosal surfaces of the respiratory tract, gastrointestinal tract and the genitourinary tract and in secretions from all secretory glands (McGhee, J. R. et al., 1983, Annals NY Acad. Sci. 409). These sIgA antibodies act to prevent colonization of pathogens on a mucosal surface (Williams, R. C. et al., Science 177, 697 (1972); McNabb, P. C. et al., Ann. Rev. Microbiol. 35, 477 (1981)) and thus act as a first line of defense to prevent colonization or invasion through a mucosal surface. The production of sIgA can be stimulated either by local immunization of the secretory gland or tissue or by presentation of an antigen to either the gut-associated lymphoid tissue (GALT or Peyer's patches) or the bronchial-associated lymphoid tissue (BALT; Cebra, J. J. et al., Cold Spring Harbor Symp. Quant. Biol. 41, 210 (1976); Bienenstock, J. M., Adv. Exp. Med. Biol. 107, 53 (1978); Weisz-Carrington, P. et al., J. Immunol. 123, 1705 (1979); McCaughan, G. et al., Internal Rev. Physiol 28, 131 (1983)). Membranous microfold cells, otherwise known as M cells, cover the surface of the GALT and BALT and may be associated with other secretory mucosal surfaces. M cells act to sample antigens from the luminal space adjacent to the mucosal surface and transfer such antigens to antigen-presenting cells (dendritic cells and macrophages), which in turn present the antigen to a T lymphocyte (in the case of T-dependent antigens), which process the antigen for presentation to a committed B cell. B cells are then stimulated to proliferate, migrate and ultimately be transformed into an antibody-secreting plasma cell producing IgA against the presented antigen. When the antigen is taken up by M cells overlying the GALT and BALT, a generalized mucosal immunity results with sIgA against the antigen being produced by all secretory tissues in the body (Cebra et al., supra; Bienenstock et al., supra; Weinz-Carrington et al., supra; McCaughan et al., supra). Oral immunization is therefore an important route to stimulate a generalized mucosal immune response and, in addition, leads to local stimulation of a secretory immune response in the oral cavity and in the gastrointestinal tract.

An "immune response" can be measured using a technique known to those of skill in the art. For example, serum, blood or other secretions may be obtained from an organism for which an "immune response" is suspected to be present, and assayed for the presence of a of the above mentioned immunoglobulins using an enzyme-linked immuno-absorbant assay (ELISA; U.S. Pat. No. 5,951,988; Ausubel et al., Short Protocols in Molecular Biology 3rd Ed. John Wiley & Sons, Inc. 1995). According to the present invention, an antigen can be said to stimulate an "immune response" if the quantitative measure of immunoglobulins in an animal treated with an antigen detected by ELISA is statistically different from the measure of immunoglobulins detected in an animal not treated with the antigen, wherein the immunoglobulins are specific for the antigen. A statistical test known in the art may be used to determine the difference in measured immunoglobulin levels including, but not limited to ANOVA, Student's T-test, and the like, wherein the P value is at least <0.1, <0.05, <0.01, <0.005, <0.001, and even <0.0001.

An "immune response" can be measured using other techniques such as immunohistochemistry using labeled antibodies which are specific for portions of the immunoglobulins raised during the "immune response". Tissue from an animal to which an antigen has been administered according to the invention may be obtained and processed for immunohistochemistry using techniques well known in the art (Ausubel et al., Short Protocols in Molecular Biology 3rd Ed. John Wiley & Sons, Inc. 1995). Microscopic data obtained by immunohistochemistry can be quantitated by scanning the immunohistochemically stained tissue sample and quantitating the level of staining using a computer software program known to those of skill in the art including, but not limited to NIH Image (National Institutes of Health, Bethesda, Md.). According to the present invention, an antigen of the present invention can be said to stimulate an "immune response" if the quantitative measure of immunohistochemical staining in an animal treated with an antigen is statistically different from the measure of immunohistochemical staining detected in an animal not treated with the same antigen, wherein said histochemical staining requires binding specific for that protein. A statistical test known in the art may be used to determine the difference in measured immunohistochemical staining levels including, but not limited to ANOVA, Student's T-test, and the like, wherein the P value is at least <0.1, <0.05, <0.01, <0.005, <0.001, and even <0.0001.

As used herein, "Langerhans cells" refers to bone marrow-derived, antigen-processing and -presenting cells that are involved in a variety of T cell responses. These cells have dark nuclei and pale, or clear cytoplasm, no desmosomes attaching to neighboring cells, no tonofilament bundles and no melanosomes. However, they do contain smooth vesicles, multivesicular bodies, and lysosomes, but most characteristic are the Birbeck granules. Langerhans cells are present in the basal, spinous and granular layers of the skin, but are also found in other squamous epithelia, including the oral cavity, esophagus, and vagina, as well as in lymphoid organs such as the spleen, thymus, and lymph node.

As used herein an "activated Langerhans cell" refers to Langerhans cells that have phagocytosed antigens and are increased their expression of major histocompatibility complex class I or II and costimulatory molecules and will migrate to T cell areas of draining lymph nodes. Activated Langerhans cells undergo a maturation process that allows them to become stimulators of T cell immunity. As used herein a "mature Langerhans cell" refers to cells that have gained potent immunogenic capacity, including the ability to secrete T-cell attracting chemokines and to interact with T-cells. They are characterized as having the properties of being CD24+, CD25+, CD69−, CD80 (B7-1)+, CD83+, CD122+ and CCR7+. It is understood that not all cells necessarily express, or do not express, detectable levels of all of the markers listed. Mature Langerhans cells lose the capacity to phagocytose antigen. Differences in types of Langerhans cells can be detected with standard immunohistochemistry assays.

As used herein, "identifying" as it refers detecting indicators that a subject that is susceptible to a condition refers to the process of assessing a subject and determining that the subject is at risk of developing or could develop a condition. A subject can be susceptible to a condition due to environmental conditions (e.g., population density, availability of clean water, hospitalization), genetic predisposition (e.g., heritable immune deficiency), the presence of other condition (e.g., burns or other injury in which the skin is disrupted, cystic fibrosis, AIDS), or the treatment of conditions with drugs that result in immunodeficiency (e.g., cancer chemotherapeutic agents).

As used herein, "selecting" refers to the process of determining that an identified subject will receive an agent to prevent or treat the occurrence of a condition. Selecting can be based on an individuals susceptibility to a particular disease or condition due to, for example, family history, lifestyle, age, ethnicity, or other factors.

"Measuring" means detecting or determining the amount, for example, any one of an increase or a decrease in immunogenicity, an increase in an immune response, an increase in the concentration of Langerhans cells at the site or irradiation, an increase in the maturation or activation of Langerhans cells, an increase in the number of mature Langerhans cells, an increase in the production of Heat Shock Proteins (HSPs), an increase in the secretion of HSPs, an increase in cell membrane permeability, an increase in the level of one or more cytokines or chemokines, an increase in antibody titer to an agent, or an increase in lymphocyte cytotoxic activity, according to the methods described herein. Measuring is the steps taken to determine if an increase or decrease in a level of the material to be detected. Measuring may indicate a level that is zero or below the level of detection, or greater than the linear detection limit of the method used for measuring.

"Measuring" according to the invention is performed in vitro or in vivo, for example in the skin at the site of laser exposure, in serum or in blood or other biological sample, tissue or organ.

"Measuring" also means detecting a change that is either an increase or decrease in the response (for example an increase in immunogenicity, an increase in an immune response, an increase in the concentration of Langerhans cells at the site or irradiation, an increase in the maturation or activation of Langerhans cells, an increase in the number of mature Langerhans cells, an increase in the production of Heat Shock Proteins (HSPs), an increase in the secretion of HSPs, an increase in cell membrane permeability, an increase in the level of one or more cytokine or chemokine, an increase in antibody titer to an agent, or an increase in lymphocyte cytotoxic activity, a decrease in the development of disease, or a decrease in the death rate in response to a pathogen challenge) of a subject to administration of an agent, according to the methods described herein.

"Measuring" is performed in a subject wherein an agent has been administered and wherein said subject has been exposed to a laser. "Measuring" is also performed in a control subject, for example a subject that has not received an agent and that has not been exposed to a laser, or a subject that has received an agent but has not been exposed to a laser.

As used herein, a "decrease" as it refers to a diminution in the level of a response as defined herein, means a response that is at least about 2-fold (for example about 2, 3, 4, 5, 10, 15, 20, 25, 30, 35, 40, 45, 50, 55, 60, 65, 70, 75, 80, 85, 90, 95, 100, 1000-fold or more) or at least about 2% (for example, about 2, 3, 4, 5, 10, 15, 20, 25, 30, 35, 40, 45, 50, 55, 60, 65, 70, 75, 80, 85, 90, 95, 99, or 100%), less than the level of response of an untreated subject, for example a subject that has not received an agent and has not been exposed to a laser or a subject that has received an agent but has not been exposed to a laser subject.

The phrase "pharmaceutically acceptable carrier" is art recognized and includes a pharmaceutically acceptable material, composition or vehicle, suitable for administering compounds used in the methods described herein to subjects, e.g., mammals. The carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. In the instant invention, suitable carriers to be administered prior to exposure to the laser preferably do not include chromophores or other compounds that alter the absorption of heat by the tissue, or result in chemical reactions that can cause significant and/or irreversible damage to the cells or tissue. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

The language "therapeutically effective amount" or a "therapeutically effective dose" of a compound is the amount necessary to or sufficient to provide a detectable improvement in of at least one symptom associated or caused by the state, disorder or disease being treated. The therapeutically effective amount can be administered as a single dose or in multiple doses over time. Two or more compounds can be used together to provide a "therapeutically effective amount" to provide a detectable improvement wherein the same amount of either compound alone would be insufficient to provide a therapeutically effective amount.

As used herein, the terms "effective" and "effectiveness" includes both pharmacological effectiveness and physiological safety. Pharmacological effectiveness refers to the ability of the treatment to result in a desired biological effect in the patient. Physiological safety refers to the level of toxicity, or other adverse physiological effects at the cellular, organ and/or organism level (often referred to as side-effects) resulting from administration of the treatment. On the other hand, the term "ineffective" indicates that a treatment does not provide sufficient pharmacological effect to be therapeutically useful, even in the absence of deleterious effects, at least in the unstratified population. (Such a treatment may be ineffective in a subgroup that can be identified by the expression profile or profiles.) "Less effective" means that the treatment results in a therapeutically significant lower level of pharmacological effectiveness and/or a therapeutically greater level of adverse physiological effects, e.g., greater liver toxicity.

Thus, in connection with the administration of a drug, a drug which is "effective against" a disease or condition indicates that administration in a clinically appropriate manner results in a beneficial effect for at least a statistically significant fraction of patients, such as a improvement of symptoms, a cure, a reduction in disease load, reduction in tumor mass or cell numbers, extension of life, improvement in quality of life, or other effect generally recognized as positive by medical doctors familiar with treating the particular type of disease or condition.

In reference to response to a treatment, the term "tolerance" refers to the ability of a patient to accept a treatment, based, e.g., on deleterious effects and/or effects on lifestyle. Frequently, the term principally concerns the patients perceived magnitude of deleterious effects such as nausea, weakness, dizziness, and diarrhea, among others. Such experienced effects can, for example, be due to general or cell-specific toxicity, activity on non-target cells, cross-reactivity on non-target cellular constituents (non-mechanism based), and/or side effects of activity on the target cellular substituents (mechanism based), or the cause of toxicity may not be understood. In any of these circumstances one may identify an association between the undesirable effects and variances in specific genes from the subject to contact with an agent ex vivo.

Also in some embodiments, the method of selecting a treatment involves selecting a method of administration of a compound, combination of compounds, or pharmaceutical composition, for example, selecting a suitable dosage level and/or frequency of administration, and/or mode of administration of a compound. The method of administration can be selected to provide better, preferably maximum therapeutic benefit. In this context, "maximum" refers to an approximate local maximum based on the parameters being considered, not an absolute maximum.

Also in this context, a "suitable dosage level" refers to a dosage level that provides a therapeutically reasonable balance between pharmacological effectiveness and deleterious effects. Often this dosage level is related to the peak or average serum levels resulting from administration of a drug at the particular dosage level.

As used herein, "cell membrane permeability" refers to a property of cell membranes that allows the passage of solvents and solutes into and out of cells. Cell membrane permeability can be measured by methods well known in the art including but not limited to spectrofluorometry, luminometry, or flow cytometry.

An increase in "cell membrane permeability" refers to an increase of at least about 2-fold (for example about 2, 3, 4, 5, 10, 15, 20, 25, 30, 35, 40, 45, 50, 55, 60, 65, 70, 75, 80, 85, 90, 95, 100, 1000-fold or more) or at least about 2% over the normal permeability of a particular cell (for example, about 2, 3, 4, 5, 10, 15, 20, 25, 30, 35, 40, 45, 50, 55, 60, 65, 70, 75, 80, 85, 90, 95, 99, or 100%), in a subject that has been exposed to a laser, as compared to an untreated subject.

According to the methods of the invention, an increase in cell membrane permeability refers to an increase that persists for a duration of about 1, 2, 3, 4, 5, 6, 7, 8, 9, 10, 20, 30, 40, 50 minutes, about 1, 2, 3, 4, 5, 6, 7, 8, 9, 10 or more hours, or about 1, 2, 3, 4, 5, 6, 7, 8, 9, 10 or more days.

As used herein, a "cytokine" refers to a class of signaling proteins and glycoproteins that, like hormones and neurotransmitters, are used extensively in cellular communication. While hormones are secreted from specific organs to the blood, and neurotransmitters are related to neural activity, the cytokines are a more diverse class of compounds in terms of origin and purpose. They are produced by a wide variety of hematopoietic and non-hematopoietic cell types and can have effects on both nearby cells or throughout the organism, sometimes strongly dependent on the presence of other chemicals. The cytokine family consists mainly of smaller, water-soluble proteins and glycoproteins with a mass of between 8 and 30 kDa. Cytokines are critical to the functioning of both innate and adaptive immune responses. They are often secreted by immune cells which have encountered a pathogen as a way to activate and recruit more immune cells and increase the system's response to the pathogen. However, apart from their role in the development and functioning of the immune system, as well as their aberrant modes of secretion in a variety of immunological, inflammatory and infectious diseases, cytokines are also involved in several developmental processes during embryogenesis.

A cytokine useful according to the invention includes but is not limited to pro-inflammatory cytokines such as IL-1 alpha, IL-1 beta, TNF-alpha, IL-6, and IL-12, as well as growth-promoting cytokines such as granulocyte-macrophage colony stimulating factor or type I and type II interferons.

As used herein, a "chemokine" refers to a family of small cytokines, or proteins secreted by cells. Proteins are classified as chemokines according to shared structural characteristics such as small size (they are all approximately 8-10 kilodaltons in size), and the presence of four cysteine residues in conserved locations that are key to forming their 3-dimensional shape. Their name is derived from their ability to induce directed chemotaxis in nearby responsive cells; they are chemotactic cytokines. Some chemokines are considered pro-inflammatory and can be induced during an immune response to promote cells of the immune system to a site of infection, while others are considered homeostatic and are involved in controlling the migration of cells during normal processes of tissue maintenance or development. Chemokines are found in all vertebrates, some viruses and some bacteria, but none have been described for other invertebrates. These proteins exert their biological effects by interacting with G protein-linked transmembrane receptors called chemokine receptors, that are selectively found on the surfaces of their target cells.

A chemokine useful according to the invention includes but is not limited to IL-8, MIP-1, MIP-2, IP-10, RANTES, CCR5, CCR6, CCR7, or CXCR4.

As used herein, "antibody titer" means a measurement of how much antibody an organism has produced that recognizes a particular epitope, expressed as the greatest dilution ratio (or its reciprocal) that still gives a positive result. In one embodiment, antibody titers are determined by ELISA assays.

As used herein, "lymphocyte cytotoxic activity" means the ability of a lymphocyte to kill another cell of a different type, typically by means of elaborating porins. This capability can be measured by co-culturing lymphocytes and target cells.

As used herein, "improving the efficiency" means increasing, as defined herein, any one of the level of response, the speed with which a response occurs, or the duration of the response, as compared to the response to an agent in a subject that has not been exposed to a laser. An increase in the efficiency refers to a change in the level of a response, the speed with which a response occurs or a duration of the response in a subject that has been exposed to a laser as compared to a subject that has not been exposed to a laser, that is at least about 2-fold more (for example about 2, 3, 4, 5, 10, 15, 20, 25, 30, 35, 40, 45, 50, 55, 60, 65, 70, 75, 80, 85, 90, 95, 100, 1000-fold or more) or at least about 2% more (for example, about 2, 3, 4, 5, 10, 15, 20, 25, 30, 35, 40, 45, 50, 55, 60, 65, 70, 75, 80, 85, 90, 95, 99, or 100% more), than the efficiency of a response in a subject that has been exposed to a laser, as compared to an untreated subject.

As used herein, a subject that is "immunocompromised" refers to a subject that has an immunodeficiency of any kind. An "immunodeficiency" (or immune deficiency) is a state in which the immune system's ability to fight infectious disease is compromised or entirely absent. Most cases of immunodeficiency are acquired ("secondary") but some people are born with defects in the immune system, or primary immunodeficiency. An immunocompromised person may be particularly vulnerable to opportunistic infections, in addition to normal infections that could affect everyone. A subject that is "immunocompromised" refers to a subject wherein the decrease in the ability of the subject to respond to an infection or infectious disease is at least about 2-fold less (for example about 2, 3, 4, 5, 10, 15, 20, 25, 30, 35, 40, 45, 50, 55, 60, 65, 70, 75, 80, 85, 90, 95, 100, 1000-fold or more) or at least about 2% less (for example, about 2, 3, 4, 5, 10, 15, 20, 25, 30, 35, 40, 45, 50, 55, 60, 65, 70, 75, 80, 85, 90, 95, 99, or 100%), than the ability of a subject that is not immunocompromised to respond to an infection or an infectious disease.

As used herein, "extracellular matrix" or "ECM" refers to the extracellular part of tissue that usually provides structural support to the cells in addition to performing various other important functions. The extracellular matrix is the defining feature of connective tissue in mammals. Extracellular matrix includes the interstitial matrix and the basement membrane. Interstitial matrix is present between various cells (i.e., in the intercellular spaces). Gels of polysaccharides and fibrous proteins fill the interstitial space and act as a compression buffer against the stress placed on the ECM. Basement membranes are sheet-like depositions of ECM on which various epithelial cells rest. The extracellular matrix comprises polysaccharides (for example, glycosaminoglycans or cellulose) and proteins (such as collagen) secreted by cells. Examples of extracellular matrix proteins include but are not limited to collagen, laminin, fibronectin, vitronectin, elastin, glycosaminoglycans, proteoglycans, and combinations of some or all of these components.

As used herein, "skin cells" are cells which make up the epidermis for example, Merkel cells, keratinocytes, melanocytes and Langerhans cells.

As used herein, "secretion" refers to the process of segregating, elaborating, and releasing a substance from a cell.

As used herein, "obtaining" is understood as purchase, procure, manufacture, or otherwise come into possession of the desired material.

"Providing," refers to obtaining, by for example, buying or making the, e.g., polypeptide, drug, polynucleotide, probe, antigen, and the like, including libraries of such compounds or libraries of combinations of types of compounds. The material provided may be made by any known or later developed biochemical or other technique. For example, compounds may be derived from natural sources, be chemically synthesized by directed or combinatorial methods, or a collection of known compounds (e.g., compounds approved for therapeutic use in humans).

As used herein, the term "recombinant DNA molecule" as used herein refers to a DNA molecule, which is comprised of segments of DNA joined together by means of molecular biological techniques.

As used herein, a nucleic acid sequence, even if internal to a larger oligonucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements which direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

Unless specifically stated or obvious from context, as used herein, the term "or" is understood to be inclusive.

Unless specifically stated or obvious from context, as used herein, the terms "a", "an", and "the" are understood to be singular or plural.

As used herein, "about" is understood to be relative to the amount of variance typically tolerated in the specific assay, method, or measurement provided. For example, "about" is typically understood to be within about 3 standard deviations of the mean, or two standard deviations of the mean. About can be understood as a variation of 20%, 15%, 12%, 10%, 8%, 5%, 3%, 2%, or 1%, depending upon the tolerances in the particular art, device, assay, or method.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

The invention provides a laser-based method of creating both photothermal and photokinetic effects in skin cells leading to enhanced immunostimulatory effects, without causing significant and irreversible cell damage. Without wishing to be bound by mechanism, it is suggested that laser treatment stimulates the extracellular release of HSP70 from cells in the skin. This requires a laser emitting light at a specific combination of wavelength, pulse duration, frequency and fluence to induce production and extracellular release of HSP70 in the epidermal and dermal layer of the skin over a relatively short exposure time without causing concomitant tissue damage.

The invention provides methods for laser-based enhancement of vaccine efficacy. Fundamentally, it utilizes a specific type of laser irradiation for an exposure duration and frequency. It is suggested that exposure to the laser under the specific parameters disclosed herein causes enough stress on cells of the epidermal and dermal layer of the skin sufficient to result in the secretion of a significant amount heat shock protein 70 molecules into the extracellular matrix, but not enough to result in irreversible cellular damage. The end result of this irradiation is the enhanced response of the epidermal immune mechanisms to administered vaccines, leading to a better immune response in the immunized subject. As an example, FIG. 1 shows the ideal ranges of pulse duration, frequency and power for an Nd:YAG laser emitting at 578 nm for use in the methods of the invention.

To create the immune enhancing effect of laser irradiation of the epidermal and dermal layers of the skin, a wavelength or combination of wavelengths of light must be selected that are significantly absorbed by one or more chromophores, which are chemical compounds capable of selective light absorbance, located in the epidermal or dermal layers of the skin. Examples of chromophores are melanin, hemoglobin, riboflavin, and cytochrome. It is suggested that this preferential absorption is the basis for the subsequent photothermal, photokinetic and photochemical effects that leads to enhanced immune response in immunized subjects.

To practice the methods of the invention, the skin must be exposed to the laser light at a site at or near the site of injection. Preferably, the site of injection is exposed to the laser. The skin can be exposed to the laser at a site near the injection site provided that the skin exposed to the laser is within the area in which the vaccine would diffuse between the time of the injection and the time of exposure to the laser.

The non-damaging laser-based methods of the invention are distinct from prior medical uses of lasers. The approved, routine medical applications of lasers have largely been methods that intentionally damage tissue including:

1) Laser surgery, in which lasers are employed to cut tissue;
2) Laser ablation or thermotherapy, in which lasers are used to destroy diseased or unwanted tissue (including hair removal and tatoo removal);
3) Laser coagulation, in which lasers are used to seal blood vessels or "weld" tissues together; and
4) Laser photodynamic therapy, in which laser light is used to alter chemical agents that produce oxygen radicals, killing abnormal cells.

All these approaches use lasers to damage or destroy tissue in some way.

The methods provided herein are not based on creating irreversible damage or destruction of cells. Instead the methods are based on exposing cells to a laser of relatively high power without causing significant or irreversible damage to the cells. Irreversible damage does not include a cell stress response in which the cell may enter a period of senescence prior to cell division. Reversible damage can be induced and detected, for example, by the activation of one or more cell cycle checkpoints which can result in a pause in the cell cycle or by the detection of a transient increase in membrane permeability.

Irreversible damage to cells can be caused by the destructive application of heat on proteins or lipids in the cell (denaturation or coagulation), by thermal expansion or vaporization of water in and around the cell (ablation), or by triggering the release of destructive chemical compounds within the cell such as radical oxygen or nitrogen species (photochemical destruction). Denaturation, coagulation and ablation are principally the result of the conversion of laser light energy into heat energy. This conversion is mediated by chromophores, which are chemical compounds capable of selective light absorbance. Once the laser energy is converted into heat via the chromophore, heat begins to dissipate into the surrounding tissue. When light energy is absorbed by the chromophore faster than it can be dissipated to the surrounding tissue, the result is an increase in the temperature within a local region. This condition is called thermal containment. By raising the temperature of a local region (which can be an organelle, a cell, or a microstructure) to a specific level for a sustained period of time, damage to or destruction of the tissue results either by alteration of the biological material of the cell or by significant and rapid heating of intra- or extracellular water.

Figure 2:
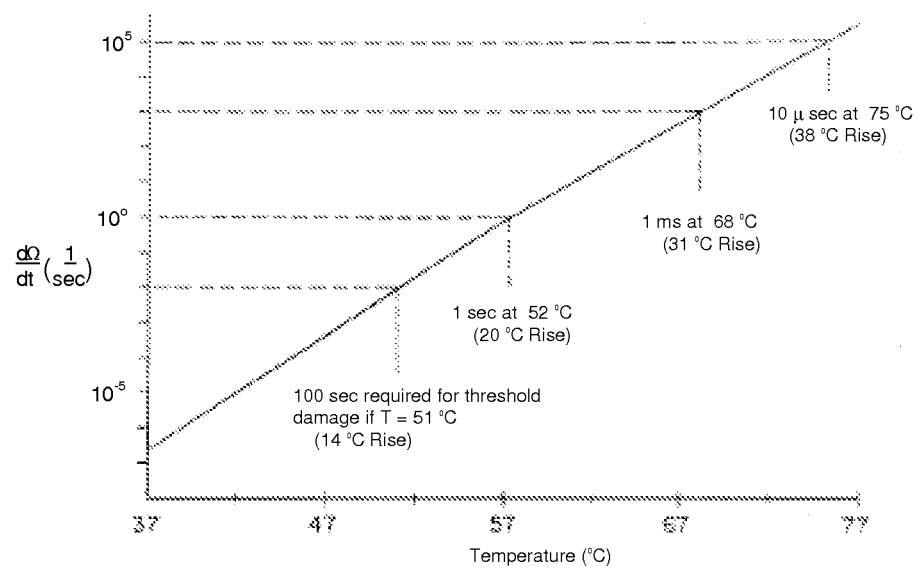
FIG. 2 shows a graph of the rates of accumulation of damage in tissue based on the rate coefficients of Henriques. Times associated with dotted lines indicate the number of seconds to achieve threshold damage for a step rise in tissue temperature.

The denaturation or coagulation of tissues (primarily proteins) occurs when a rise in temperature alters the structures within the tissue, causing a loss of function. Denaturation of proteins, for example, occurs when the kinetic energy caused by heat overcomes the weak hydrogen bonds and van der Waals interactions that help maintain the three-dimensional structure of proteins. There is an inverse relationship between temperature and time in heat-based denaturation of proteins in the skin. This relationship is illustrated in FIG. 2 showing the threshold temperature for tissue damage in the skin at different time intervals (Welch 1984).

Figure 3:
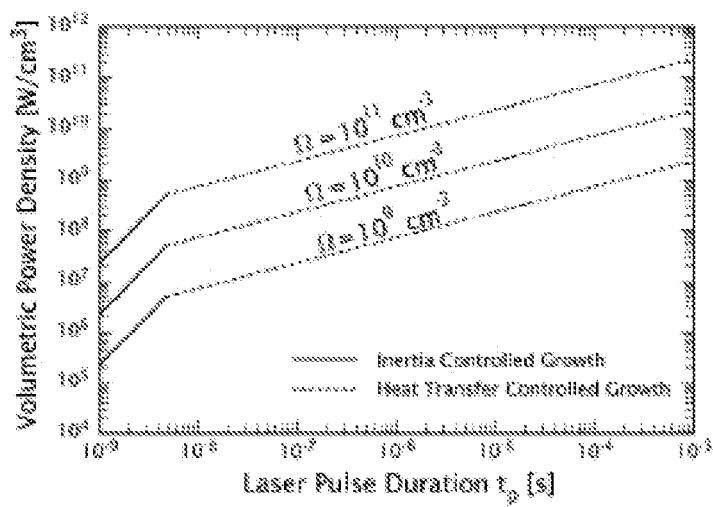
FIG. 3 is a schematic showing the relationship between power density and pulse duration in the generation of phase explosion of water in tissues using a laser.

An alternative method of causing irreversible tissue destruction is through the ablation of the tissue using thermal expansion or vaporization of water. Ablation refers to the explosive removal of tissue from the site of irradiation. In this approach, water itself is the chromophore for the laser. In laser ablation, a small volume of water is very rapidly heated to the point where either its expansion within a confined area causes a loss of the structural integrity of the tissue or cell, or to the point where the water experiences a rapid phase change into a gas, referred to as a phase explosion. In these conditions, water exists in a superheated metastable liquid state and then rapidly moves into an equilibrium state as a gas. This phase transition results in the creation of microbubbles which rapidly expand, causing mechanical disruption and removal of the local tissue. In the case where water within or around a tissue is heated more slowly, the heat is likely to be transferred into the tissue itself, resulting in the denaturing effect discussed above. The graph in FIG. 3 shows the relationship between pulse duration and power density required to generate such phase explosions (Vogel and Venugopalan 2003).

Irreversible damage to the cells can also result from the photochemical effects of lasers, which occur when laser energy catalyzes a chemical process that is toxic to the cell. One of the major ways lasers can cause cell and tissue destruction through photochemical effects is the generation of reactive oxygen or nitrogen species. The precise mechanisms of action are not understood, but it is hypothesized that when the energy of a photon from a laser exceeds the energy needed to remove an electron from a molecule, a collision with that molecule might then lead to generation of free radicals. Therefore, the initial cellular damage may be due to the local formation of hydroxyl or other reactive radicals that may then generate longer lived organic radicals including peroxy- or alkoxy-radicals (Kim 2002). Typical targets for this kind of laser damage are cell membranes, mitochondria, nitric acid complexes, proteins and lipids.

Free radicals damage cellular DNA, cell membranes, alter intracellular and extracellular redox pathways and cause denaturation of proteins within the cell. While cells have a variety of mechanisms for defending themselves against radical oxygen or nitrogen species damage, generation of larger amounts of reactive oxygen or nitrogen species can exceed the ability of the cell to respond. When the generation of free radicals within or outside of a cell exceed the ability of the cell to prevent or repair the damage, the cell is irreversibly damaged and in most cases apoptosis is induced.

Another photochemical effect is the direct damage of cellular DNA by laser light. In some cases absorption of energetic photons can cause breaks in the DNA structure, leading in some cases to irreversible cell damage and subsequent apoptosis.

Irreversible damage to cells from photothermal and photochemical effects result in either the apoptosis or necrosis of the cell, depending on the site and extent of the damage, or the disruption of the entire tissue (in the case of laser ablation). Cells need not be killed immediately upon exposure to the laser, but instead, they may die over a longer period of time as a direct result of laser treatment (e.g., initiate apoptosis, become necrotic, somatic fusion and subsequent mitotic catastrophe). The exact cause or causes of irreversible damage is not a limitation of the invention. Irreversible damage can result from a combination of mechanisms.

Thermal damage to a culture of cells or living tissue can be expressed by the parameter $\Omega$, which is the logarithm of the ratio of the concentration of the intact protein in a sample before damage and the concentration of intact protein in a sample after exposure. $\Omega$ is dimensionless, exponentially dependent on temperature, and linearly dependent on time of exposure (Diller and Pearce 1999). Calculation of $\Omega$ is a function of the ratio of the concentration of viable cells at time point 0 and at time point (t). A value of 1 for $\Omega$ at the time point (t) means that 63.2% of cells in a given sample have been damaged at that point, while a value of 10 means that virtually all cells in the sample have been destroyed.

Measurement of the concentration of viable cells in a particular tissue or culture is routine in the art. Methods and kits are known in the art to detect apoptosis and necrosis. The number of cells undergoing apoptosis or necrosis can be readily scored and expressed as a percentage of cells exposed to the laser.

Apoptosis can be detected using flow cytometry techniques. For example, apoptotic cells show an increased uptake of the vital dye HO342 compared to live cells due to a changes in membrane permeability. Apoptosis can be measured using a number of other assay-based approaches including measurement of DNA fragmentation, membrane phospholipid changes, interleukin-1beta converting enzyme-like protease activation, or nucleosomal fragmentation by DNA agarose gel electrophoresis. Finally, apoptosis can be detected through visual means such as changes in cell morphology.

Necrotic cells can be detected by flow cytometry techniques, such as the addition of the nucleic acid stain PI, which binds to DNA or RNA but cannot permeate cell membranes and therefore is visible under fluorescence only if the cell membrane has been compromised, or stains such as propidium iodide or 7-AAD that discriminate cells which have lost membrane integrity. In addition, they can be visualized optically using standard staining and microscopy techniques.

The degree of irreversible damage to tissue samples may also be determined by several methods known in the art, such as the measurement of changes in optical characteristics of the tissue. For example, concentration of viable cells in muscles and collagen can be measured by the relative birefringence of tissue when viewed through a polarized filter (Diller and Pearce 1999), Undamaged tissue is birefringent and appears bright while damaged, nonbirefringent tissue is dark. The proportion of damaged to undamaged tissue in a particular sample can be calculated by measuring optical intensity. Other methods of optical measurement are also possible (see for example Roggan and Müller 1995).

Additional methods exist in the art to quantify damage in tissue includes enzyme deactivation (Bhowmick and Bischof 1998) and extravasation of fluorescent-tagged proteins (Green and Diller 1978).

The method of this invention utilizes high power laser irradiation of tissue, but is designed to avoid significant and irreversible damage to cells. Preferably less than 1% of cells are irreversibly damaged upon laser exposure using the methods of the invention, which would correspond to an $\Omega$ value of 0.01 or less. In an embodiment, significant and irreversible damage of the cells is limited or prevented by limiting the increase in temperature in the cells and/or tissues exposed to the laser in the methods of the invention to below the levels below the critical thresholds illustrated in FIG. 2. In addition, the method does not result in the heating of intracellular or extracellular water to supercritical temperatures required for vaporization.

Finally, the method is distinguished from the use of relatively low power laser irradiation to modify the metabolic activity of cells in order to accelerate burn or wound healing. Such methods, which are sometimes referred to as low-level laser therapy (LLLT) use very low power irradiation (in the range of 10 milliwatts to 10 watts) with a wide variety of wavelengths, pulse durations and frequencies with the intention of stimulating the production of factors such as proangiogenic or other growth factors that can lead to accelerated healing processes. These approaches are intended to cause almost imperceptible changes in the temperature of the cells subject to such lasers. LLLT is controversial and the preclinical and clinical evidence of its effectiveness is mixed (Posten et al. 2005).

Principles of Laser Effects in the Skin

The effect of lasers on skin tissue depends on several variables. First, the wavelength of laser light determines the depth of its penetration into the skin. Laser light of wavelengths in the near infrared spectrum penetrate furthest into the skin. Absorption of laser light by surrounding tissues also depends on the wavelength of the laser used. For example, visible light laser radiation is absorbed by pigments in the skin (chromophores). Absorption by a particular pigment is dependent on the laser's wavelength. Near infrared energy, such as that produced by the neodymium: yttrium aluminum garnet (Nd:YAG) laser at 1.06 µm, has little pigment specificity, while the 10.6 µm wavelength light emitted by the $CO_2$ laser is effectively absorbed by water. Other important laser parameters that determine the response of skin cells are beam size (cm), pulse duration (seconds), power (watts/cm) and fluence (J/cm$^2$). An additional set of effects can be created through the use of laser pulses at an appropriate frequency (Hz, or KHz). The methods herein rely predominantly on the use of a combination of the desired pulse length, preferably in the nanosecond range; frequency, preferably in the kilohertz range; and power, preferably in the range of about 1-10 watts. These parameters are balanced to promote one or more of increased local concentration of HSP 70 at or near the site of laser exposure, particularly extracellular HSP 70, increased local concentration or number of Langerhans cells at or near the site of exposure, and/or increased response to antigen as compared to a subject not exposed to laser, without causing significant or irreversible damage to the cells or tissue exposed to the laser. The method is practiced to minimize the exposure time required to yield these effects to seconds or minutes. Variation in wavelength, laser type, beam size, fluence, and frequency of laser administration on a macro time scale (e.g., minutes, hours, days, rather than fractions of seconds) is well within the ability of those in the art. Methods of testing specific parameters using the methods provided herein as well as those known to those of skill in the art is routine.

Photothermal Effects

The absorption of laser energy by pigments within skin cells results in conversion of some of the light energy into heat. Exposure of skin to laser beam over a period of time will result in the generation and diffusion of heat through the surrounding tissues, resulting in a local temperature gradient. These gradients are highly predictable and reproducible, making it possible to carefully adjust the amount of heat generated in the skin (Reinisch 2003, incorporated herein by reference). By using a sufficiently powerful laser of a specified wavelength for a sufficient duration of exposure, a volume of the skin can convert laser light to heat faster than it can be diffused away—a condition known as thermal containment. Under such conditions, tissue can be heated to a supraphysiologic level, eventually leading to significant and irreversible cell injury, death or destruction of tissue through superheating of water within and around the tissues (Venugopalan et al. 1996, incorporated herein by reference). Because cellular injury or death is a property of the heat exposure duration and not solely of the temperature (Moritz and Henrique 1947, incorporated herein by reference), the heating effect of a laser can be controlled to keep it below a level that causes significant cell damage or death. This heating effect leads to two biological processes in the skin which together create the conditions for effective immunostimulation suitable for enhancing vaccination: production and secretion of heat shock proteins and concentration stimulation of Langerhans cells.

Photomechanical Effects

Under specific conditions, some energy of the light can be converted into kinetic energy. The use of a pulsed laser light source with the proper configuration is capable of generating a shock wave in a volume of local tissue (e.g., Doukas et al. 1996). These photomechanical effects can eventually result in disruption or destruction of cells. However, under carefully controlled conditions, laser pulses can simply lead to permeabilization of cellular membranes (Lee et al. 1996, incorporated herein by reference). This permeabilization enables passage of substances into and out of the cell (e.g. Flotte et al. 1993, 1995; Lee et al. 1996; McAuliffe et al. 1997; Mulholland et al. 1999). The effects of permeabilization typically lasts for several minutes. Practical applications of this phenomenon are being examined for delivery of drugs and other substances into the cell, including chemotherapeutic agents, interfering RNA and gene constructs (Miyamoto et al. 2003; Terakowa et al. 2004; Tang et al. 2006).

Several of these experiments have demonstrated that permeabilization increases efflux of substances from the cell. This permeabilization is capable of leading to a significant increase in the secretion of HSP70 that has been synthesized in response to heat shock. The right laser system is capable of combining photothermal and photomechanical effects, leading to significant immunostimulation in the skin.

Immunostimulation Through Heat Shock Synthesis and Release

Heating the skin at supraphysiologic levels results in the mobilization and overproduction (or overexpression) of heat shock proteins (HSPs) by skin cells (heat shock response). In general, cells produce HSPs in response to stress caused by heat, poisons or signals from nerves or hormones. There are five major groups of HSPs found in humans based on molecular size: 20-30, 50-60, 70, 90, and 100-110 kDa (Minowada and Welch 1995). Within the cell, heat shock proteins play an important protective role against these stresses, specifically assisting in protein maintenance, folding, chaperoning and degredation. and, when expressed on the surface of the cell, assist with the stabilization of the cell membrane.

Extracellularly, heat shock proteins, in particular the 70 kDa HSP70, have several positive effects on immune function. While HSP70 is involved in protein folding and chaperoning activities inside the cell, outside the cell it acts as a chaperone of protein antigens to dendritic cells and stimulates their maturation (Bendz et al. 2007). Dendritic cells are key actors in the immune response against both infectious pathogens and cancerous tumors (Banchereau and Steinman 1998). In an immature state, dendritic cells capture and process antigens with high efficiency. After maturation, they migrate to lymphoid organs to present these antigens, as well as co-stimulatory molecules, to T cells. Approximately 40% of the body's antigen-presenting dendritic cells are located in the skin. These antigen presenting cells, called Langerhans cells, are concentrated in the in the basal, spinous, and granular layers of the epidermis, showing a preference for the suprabasal portion of the epidermis.

Figure 4:
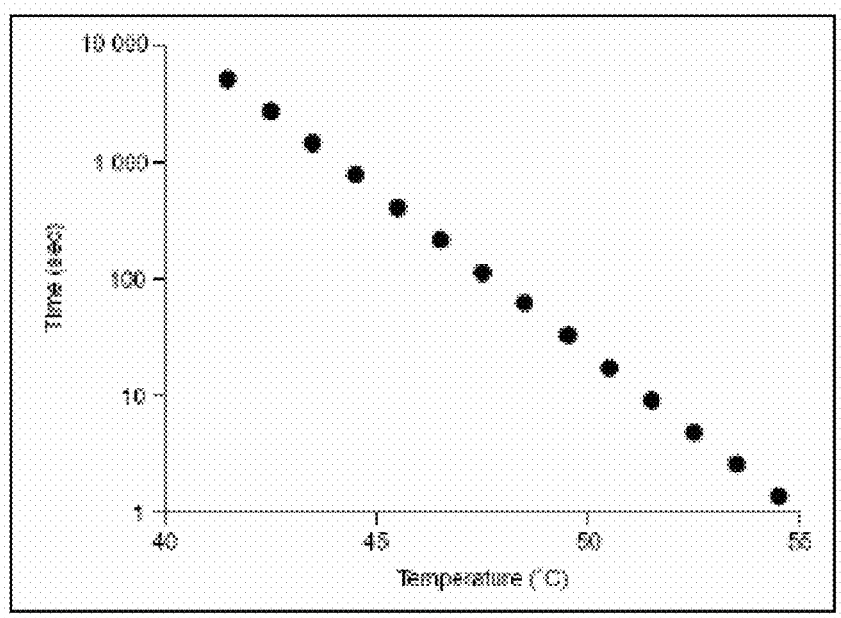
FIG. 4 is a graph showing the logarithmic relationship between temperature and exposure time for induction of a heat shock response in tissue.

There is in general a logarithmic relationship between the duration of exposure to a heat source and the temperature rise needed for synthesis and expression of HSPs (FIG. 4, Capon and Mordon 2003). Thus, long-term heating at lower temperatures results in higher rates of HSP70 synthesis (Ostberg et al. 2000), while short, intense exposure to heat can have the same effect (Law 1981). Synthesis of HSP70 can also be elicited by use of a laser capable of creating thermal confinement sufficient to raise temperatures of cells above normal but below the critical temperature where cells begin to die (Souil et al. 2001). In addition, cells vary in their ability to produce HSPs. For example, keratinocytes in the skin highly express HSP70 relative to other cell types (Trautinger et al. 1993)

While it is well-known that heat results in the increased expression of HSP70 within the cell, several investigators have shown that the application of heat can also lead to secretion of greater quantities of HSP70 outside of viable cells (Hightower and Guidon 1989; Guzhova et al. 2001; Broquet et al. 2003). Just as cells vary in their ability to express HSP70, they also differ in their ability to secrete HSP70. Some cancer cells and some specialized cells such as glial cells are able to secrete HSP70 at a much higher quantities. A number of hypotheses for the mechanism of secretion have been proposed, including transport by lipid rafts (Broquet et al. 2003), small vesicles (Lancaster and Febbraio 2005), secretory granules (Evdonin et al. 2006) or through an endolysosomal compartment (Mambula and Calderwood 2006). Research conducted by Evdonin et al. (2006) showed that heating of skin keratinocyte cells resulted in secretion of HSP70 through vesicular transport at the initial stages of heating.

This method utilizes a laser to rapidly and non-destructively (i.e., without significant or irreversible damage) cause the secretion of significant quantities of HSP70 in the skin and yield enhancements in the response to vaccination. Several investigators have previously shown that lasers of different types can enhance the expression of heat shock protein in living tissues without causing significant damage to the living cells (Ferrando et al. 1993; Desmettre et al. 2001; Souil et al. 2001; Emohare et al. 2004). To date, no research has demonstrated that a non-destructive exposure to laser irradiation leads to enhanced secretion of HSP70 from cells. More specifically, no research has demonstrated that such irradiation of cells commonly found in the epidermal and dermal layers of the skin, such as keratinocytes, enhances the secretion of HSP70 into the extracellular matrix. Finally, no research to date has established that a non-destructive laser treatment of epidermal or dermal cells will result in a significantly enhanced immune response of the skin to vaccination. Without being bound by mechanism, the approach described below demonstrates that a brief exposure of the skin to a laser with the proper combination of working characteristics leads to enhanced and rapid secretion of HSP70 by skin cells and a significant improvement in response to vaccination without causing significant irreversible damage to the irradiated cells.

Recruitment of the Langerhans Cells

The secretion of HSP70 introduces a significant additional number of chaperone proteins into the surrounding epidermal tissues that are capable of enhancing presentation the protein antigens from a vaccine to Langerhans cells. HSP70 is capable of inducing maturation of immature Langerhans cells, rapidly multiplying the number that migrates to the lymph system, where they prime T-cells to mount an immune response against a cell or virus expressing the vaccine antigen.

Figure 5:
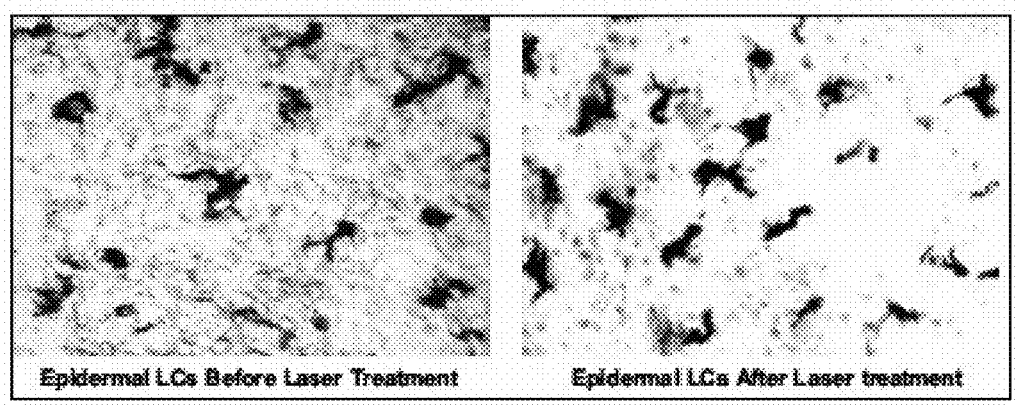
FIG. 5 shows tissue sections stained to detect the presence of Langerhans cells in the skin before and after laser treatment.

Additionally, this invention leads to the concentration of immature Langerhans cells in the local area of the skin subject to laser irradiation. FIG. 5 shows a specific example of the increase in number of Langerhans cells in the epidermal tissues of a mouse subject to laser irradiation. This concentration also serves to increase the effectiveness of vaccination by increasing the number of Langerhans cells available to receive vaccine antigens and migrate to the lymph system after maturation.

It is suggested that the concentration of Langerhans cells in the area of laser irradiation brings them into proximity with the elevated levels of secreted HSP70 proteins, leading to an acceleration and augmentation of the processes of antigen uptake, Langerhans cell maturation, and migration of activated Langerhans cells toward the lymphatic system. This production of heat shock proteins and concentration of Langerhan cells in the same area in the skin is suggested to make laser stimulation of the skin a powerful adjuvant approach that is not burdened by the kind of safety issues that plague current vaccine adjuvants.

EXAMPLES

Cu laser parameters used Examples 1-8: Exposure Diameter (cm)-0.5-1.0; Wavelength (nm)-510+578, Power (Watts)-1.0 Pulse Duration (ns)-10, Frequency (KHz)-20

Example 1: Secretion of HSP70 in Response to the Cu Laser Treatment In Vitro

Fibroblasts cells derived from mouse embryo were cultured in the Petri dish using the Eagle or No. 199 medium for 24 h. Cell culture was exposed to the light beam of the Cu laser. The levels of HSP70 have been determined before and after irradiation using antibodies to Hsp70 (Russian Patent No. 2242764 Jul. 8, 2003. After a 1 minute exposure, the separated supernatant solution displayed 350% increase of the extracellular HSP70, from 3.2 to 11.2 ng/L. The culture cells remained viable after laser irradiation as established by staining with the toluidine blue 0.2%

Example 2: Effects of the Cu Laser Irradiation on the Skin In Vivo

Figure 6:
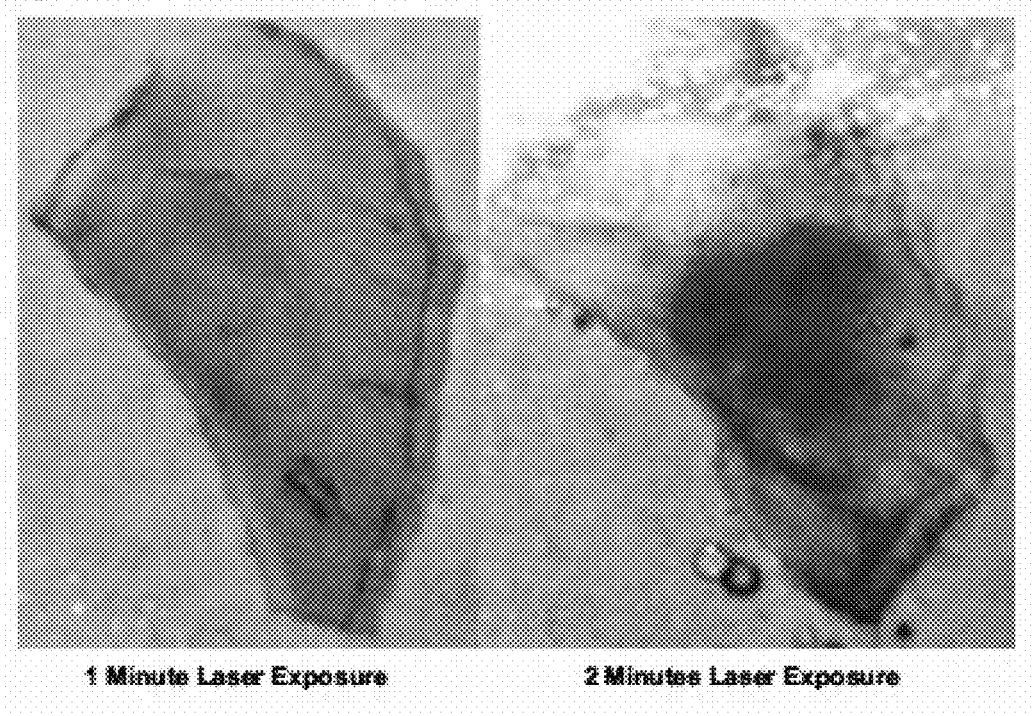
FIG. 6 shows changes in the amount of heat shock protein 70 in murine ear sheets after a one or two minute exposure to laser irradiation.
Figure 7:
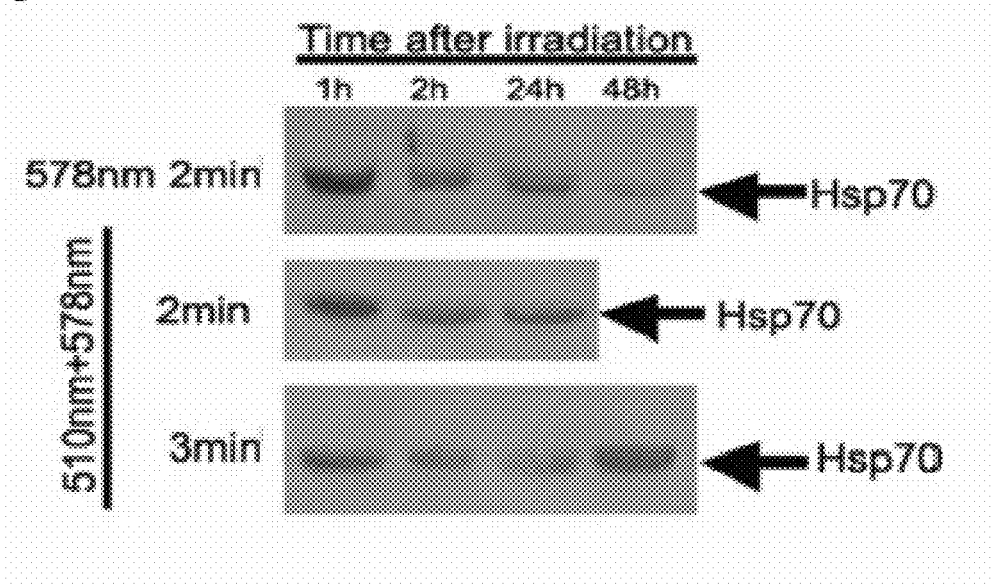
FIG. 7 shows immunoblotting results for HSP70 in epidermal cells derived from the ears of mice showing changes in total HSP in response to different combinations of laser light wavelengths and durations of exposure.

Healthy white mice (CBA, Rappolovo, 50 animals) were treated using Cu laser by exposing a section of an ear to the laser light with a diameter of 5 mm over a period of 1-3 min. After the experiments, the animals were sacrificed at different time points. Immunohistochemical staining using antibodies to HSP70 (Russian Patent No. 2242764, Jul. 8, 2003) of the ventricular epidermal sheets of the ear (FIG. 6) provided a qualitative estimate of the increased levels of the secreted HSP70 as compared to the tissue from untreated ear from the same animal. These data were supported by the results of immunoblotting analysis of the processed ventricular epidermal sheets tissues though these results did not differentiate between secreted and intracellular HSP70. Immunoblotting for HSP70 showed that the combination of the two different wavelengths of light increased the quantity and duration of HSP70 secretion over single wavelengths, and that this effect was also exposure-dependent (FIG. 7). Stimulation of the skin with laser energy from the system also resulted in the attraction of Langerhan cells into the irradiated location as determined by the tissue staining and optical microscopy (FIG. 5). At peak, the number rose from 280 to 1350 Langerhans cells per $mm^2$. Exposure of the skin to the laser irradiation was safe and did not produce any visible and microscopic signs of the burn injury and tissue de-epithelization resulting only in very mild intermittent hyperemia confined to the exposure area.

Example 3: Enhanced Antibody Production in Response to Vaccine Administered with Cu Laser In a group of 125 healthy white mice (CBA, Rappolovo), 50 animals received 50 μL of a commercial H3N2 influenza vaccine (VAXIGRIP®, Aventis Pasteur) by subcutaneous injection to the left ear and served as a control group. In an experimental group, 50 mice were administered the same vaccine together with laser treatment (Cu laser at 578/511 nm, 1-3 ns pulses at 10 MHz) of the left ear. Of the 50 animals treated with laser, a subgroup of 25 animals was a subject of a one minute exposure whereas another subgroup of 25 mice was a subject of a two-minute exposure. An additional experimental set of 25 mice received the vaccine and exogenous bovine HSP70 (10 μg per injection, dissolved in 50 μL saline solution). The animals were sacrificed and antibody titers were measured 28 days after vaccination following a standard literature protocol ["The immune drugs for grippe prophylactic and diagnostic effectiveness testing methods" Russian Federal Methodologic Standarts—MY 3.3.2.1758-03" (Sep. 28, 2003)]. Results of the experiment are summarized in the Table 1. The most optimal treatment consisted in using vaccine and laser treatment for 2 min that resulted in 86% increase of the antibody titers as compared to vaccine alone. 1 min exposure was also effective providing a 54% increase in titers. Consistent with our hypothesis about the role of HSP in improved presentation of the vaccine antigens, combination of the influenza vaccine with exogenous HSP70 produced as much as 68% increase in the antibody titers.

TABLE 1

| Antibody titers 28 days after vaccination (log2 (M ± 2 m)) | | | |
|---|---|---|---|
| Vac. alone | Vac. + Laser (1 min) | Vac. + Laser (2 min) | Vac. + HSP70 |
| 2.8 ± 0.3 | 4.3 ± 0.3 | 5.2 ± 0.4 | 4.7 ± 0.35 |

Example 4: Enhanced Survival to Lethal Challenge in Response to Vaccine Administered with Laser In a lethal challenge study in 50 mice, 15 mice received a commercial H3N2 influenza vaccine (VAXIGRIP®, Aventis Pasteur) by subcutaneous injection to the left ear (50 μL). Fifteen mice received the same dose of a vaccine with simultaneous laser treatment to the ear, whereas 20 mice in the control group were not vaccinated. All mice received a lethal dose of the H3N2 influenza virus (strain A/Aichi/2/68) by inhalation using a "Mussson" type ultrasound inhalator coupled with special murine inhalation mask 14 days post-vaccination. In a control group, only 1 mouse survived as compared to 5 animals out of 15 in the vaccinated group. The survival rate was the highest in the group that received a vaccine along with the laser adjuvant. In this group, 10 of 15 animals survived.

Example 5: Stimulation of Response to Flu Vaccine in Immunocompromised Humans with Laser Treatment In a three-arm study, the first group of 22 immunocompromised patients received a standard influenza vaccination (VAXIGRIP®, Aventis Pasteur), the second group of 22 immunocompromised patients received vaccination after a one-minute laser exposure of the skin. In the third group, 22 healthy control subjects received standard vaccination. Seven different measurements of immune function and activity were assessed 30 days after immunization. Results were normalized to the set of vaccinated healthy adults. Based on an overall assessment of all measurements, 75% of the healthy patients had a significant response to the vaccine whereas only 25% of the vaccinated immunocompromised patients had a significant response. In comparison, over 50% of the immunocompromised patients receiving vaccination with laser showed significant response: double that of the vaccine only group. Within individual measurements, antibody titers of immunocompromised patients receiving laser treatment and vaccine was 90% of that of normal controls, compared to only 50% for the vaccination only group. Exposure of the skin to laser irradiation was safe and did not produce any visible or microscopic signs of burn injury. Tissue deepithelization resulted only in very mild intermittent hyperemia confined to the exposure area. The residual skin cell infiltrates that were typically formed within 24 h following the laser treatment subsided after 5-7 days.

Example 6: Stimulation of Response to Hepatitis B Vaccine in Immunocompromised Humans with Laser Treatment In a control group, eight patients who were documented non-responders to prior administration of the hepatitis B vaccine (Recombinant Yeast Hepatitis B vaccine, Combiotech, Russia) received three hepatitis B vaccination (at 0, 1 and 3 months) coupled with weekly injections of IL-2 (2,500,000 IE SQ) (12 injections). In a study group, nine patients received the same vaccination schedule coupled with the copper laser treatment of the skin at the time of injection (power-1.5 watts, exposure time 2 minutes, vaccine injection 5 minutes after laser skin treatment). Responders were determined by the level of protective antibodies titer (>10 IE/ml). Seven of the nine patients in the laser+vaccine group achieved protective levels of hepatitis antibody whereas there were no responders in the vaccine+IL-2 group. Exposure of the skin to the laser irradiation was safe and did not produce any visible or microscopic signs of burn injury. Tissue deepithelization resulted only in very mild intermittent hyperemia confined to the exposure area.

The residual skin cell infiltrates that were typically formed within 24 h following the laser treatment subsided after 5-7 days.

Example 7: Combinations of Parameters for Immunostimulation

Various combinations of exposure diameter, wavelength, power, pulse duration, and frequency were tested for their ability to produce secretion of HSP70 in vitro and to stimulate an immune response in vivo. The results are provided in Table 2.

TABLE 2

| Laser Type | Exposure Diameter (mm) | Wavelength (nm) | Power (Watts) | Pulse Duration (ns) | Frequency (KHz) | In Vitro HSP Secretion | In Vivo Immune Response |
|---|---|---|---|---|---|---|---|
| Copper Vapor | 3-5 | 511 | 1-3 | 10-20 | 10-20 | Yes | yes |
| Copper Vapor | 3-5 | 578 | 2-5 | 10-20 | 10-20 | Yes | yes |
| Copper Vapor | 3-5 | 511/578 | 1-3 | 10-20 | 10-20 | Yes | Yes |
| Carbon Dioxide | 3-5 | 10,000 | 25-50 | 1000-3000 | 0.001-0.05 | yes | N/A |
| Semiconductor | 3-5 | 830 | 2-5 | 5-10 | 20-50 | yes | N/A |
| Semiconductor | 3-5 | 1064 | 1-5 | 5-20 | 10-50 | Yes | N/A |

Example 8: Protection of the Elderly in Annual Influenza Vaccination

In this study on the effect of laser vaccine adjuvant on protection of older individuals from seasonal influenza, healthy adults ages 65 and over are randomized into three different study arms. Arm 1 subjects receive the standard of care—intramuscular vaccination with the influenza vaccine manufactured to provide prophylaxis against the current season's influenza strain. Arm 2 subjects receive the same vaccine in an intradermal delivery (e.g., intradermal microinjection system, Becton, Dickinson & Company). Intradermal dosage is adjusted appropriately to site of delivery. Arm 3 subjects receive the same vaccine in an intradermal dosage coupled with a short-duration exposure to a laser vaccine adjuvant device immediately before administration of the vaccine. The time of laser exposure is about one minute, but may be adjusted to match skin color, and patients with darker skin receive shorter duration of irradiation. Sufficient numbers of patients are enrolled in each arm to ensure sufficient statistical powering at the end of the study, and enrollees in each arm are case-matched demographically. Enrollment is conducted at the start of the influenza season (November to May).

After 30 days, blood samples are drawn from each patient and assessed for influenza antibody titers and ELISPOT is performed to assess the number of Granzyme B-secreting cells.

Patients are followed over the influenza season (approximately 6 months) and statistics are recorded for clinical activity related to influenza (clinical visits, emergency room visits, hospitalizations, etc.).

The study shows that combination of laser irradiation and epidermal vaccination is statistically superior to both standard of therapy vaccination and epidermal vaccination alone in the improvement of antibody titers and the concentration of Granzyme-secreting cells, and that patients receiving both the epidermal vaccination and laser treatment have a statistically significant decrease in clinical events related to influenza, particularly with respect to hospitalization.

Example 9: Dose-Sparing in Avian Influenza Vaccination

In this study of the dose-sparing effects of the laser-based adjuvant when combined with both regular vaccination and with modified (epidermal) vaccination against the avian influenza vaccine (H5N1 vaccine, Sanofi Aventis), groups of healthy mice are randomized into four major groups. Mice in group 1 receive the standard intramuscular avian influenza vaccine. Mice in group 2 receive the standard avian influenza vaccine administered epidermally in the ear. Groups 1 and 2 act as control groups for the experiment.

Preliminary experiments are used to establish the doses of the vaccine for each group that correspond to protective levels of H5N1 antibody.

Mice in group 3 receive the standard avian influenza vaccine by intramuscular injection coupled with a short-duration laser exposure immediately before administration of the vaccine. Mice in group 4 receive the standard avian influenza vaccine administered using epidermal vaccination to the ear coupled with a short-duration exposure to a laser vaccine adjuvant device immediately before administration of the vaccine. The duration of laser exposure in groups 3 and 4 will be approximately one minute. Mice in group 3 are shaved in the area of intramuscular injection to maximum effect of the laser.

Within groups 3 and 4, smaller groups are selected for titration of vaccine dose, with subgroups receiving either 0.5, 0.25, 0.125 and 0.0625 times the dose of their matched control groups. The quantity of mice in each group and subgroup are adequate to sufficiently power the study for statistical analysis.

After 30 days, blood samples are drawn from each mouse and assessed for H5N1 antibody titers.

The study shows that the combination of either intramuscular or epidermal vaccination with laser irradiation allows for a significant decrease in the dosage of vaccine required to elicit protective levels of antibodies as compared with non-irradiated vaccinated controls.

Example 10: Potentiation of a DNA Vaccine

A population of healthy individuals is assessed for the difference in response to a novel DNA-based Hepatitis B vaccine compared with an existing, approved hepatitis B vaccine (RECOMBWAX HB®, Merck and Co.). Subjects are randomized to receive either the DNA-based hepatitis B vaccine, the hepatitis B vaccine combined with laser vaccine adjuvant, or the standard hepatitis B vaccine. Administration of each type of vaccine, including dosage, frequency of vaccination, and methods of administration, follows FDA-approved approaches. The time of exposure to the laser is about one minute, but may be adjusted to match skin color, and patients with darker skin receive shorter duration of irradiation. Sufficient numbers of patients are enrolled in each arm to ensure sufficient statistical powering at the end of the study, and enrollees in each arm are case-matched demographically. Exclusion criteria for the study includes previous exposure to either the hepatitis B vaccine or hepatitis B.

After completion of the vaccination period, blood samples are drawn from each patient and assessed for hepatitis B surface antigen levels.

The study shows that combination of laser irradiation and DNA vaccination yields statistically significant improvement in antibody titers over DNA vaccination alone and is statistically equivalent or superior to FDA-approved subunit vaccination.

Example 13: Potentiation of a Recombinant Subunit Vaccine

A population of healthy individuals is assessed for the difference in response to a novel subunit-based MMR (measles, mumps, rubella) vaccine compared with an existing, approved MMR vaccine that is composed of attenuated live viruses (MMR II®, Merck and Co.). Subjects are randomized to receive either the subunit-based MMR vaccine, the subunit MMR vaccine combined with laser vaccine adjuvant, or the standard MMR vaccine. Administration of each type of vaccine, including dosage, frequency of vaccination, and methods of administration, follows FDA-approved approaches. The time of exposure to the laser is about one minute, but may be adjusted to match skin color, and patients with darker skin receive shorter duration of irradiation. Sufficient numbers of patients are enrolled in each arm to ensure sufficient statistical powering at the end of the study, and enrollees in each arm are case-matched demographically. Exclusion criteria for the study includes previous vaccination against or exposure to measles, mumps, or rubella.

After completion of the vaccination period, blood samples are drawn from each patient and assessed for seroconversion against measles, mumps and rubella.

The study shows that combination of laser irradiation and subunit vaccination yields statistically significant improvement in antibody titers over subunit vaccination alone and is statistically equivalent or superior to FDA-approved subunit vaccination.

Example 12: Potentiation of a Synthetic Peptide Vaccine

A population of healthy individuals is assessed for the difference in response to a novel synthetic peptide vaccine against bacterial meningitis compared with an existing, approved bacterial meningitis vaccine that is composed of meningococcal polysaccharides conjugated to the diphtheria toxoid (MENACTRA®, Sanofi Pasteur). Subjects are randomized to receive either the synthetic peptide vaccine, the synthetic peptide vaccine combined with laser vaccine adjuvant, or the standard conjugated vaccine. Administration of each type of vaccine, including dosage, frequency of vaccination, and methods of administration, follows FDA-approved approaches. The time of exposure to the laser is about one minute, but may be adjusted to match skin color, and patients with darker skin receive shorter duration of irradiation. Sufficient numbers of patients are enrolled in each arm to ensure sufficient statistical powering at the end of the study, and enrollees in each arm are case-matched demographically. Exclusion criteria for the study includes previous vaccination against or exposure to bacterial meningitis.

After completion of the vaccination period, blood samples are drawn from each patient and assessed for seroconversion against bacterial meningitis.

The study shows that combination of laser irradiation and synthetic peptide vaccination yields statistically significant improvement in antibody titers over peptide vaccination alone and is statistically equivalent or superior to FDA-approved conjugated vaccination.

While this invention has been particularly shown and described with references to preferred embodiments thereof, it will be understood by those skilled in the art that various changes in form and details may be made therein without departing from the scope of the invention encompassed by the appended claims.

REFERENCES

Aguilar J C, Rodríguez E G. Vaccine adjuvants revisited. *Vaccine* 2007; 25:3752-3762.

Almeida-Lopes L, Rigau J, Zangaro R A, Guidugli-Neto J, Jaeger M M. Comparison of the low level laser therapy effects on cultured human gingival fibroblasts proliferation using different irradiance and same fluency. *Lasers Surg Med* 2001; 29:179-184.

Banchereau J, Steinman R M. Dendritic cells and the control of immunity. Nature 1998; 392:245-252.

Banchereau J, Briere F, Caux C, Davoust J, Lebecque S, Liu Y-J, Pulendran B, Palucka K. Immunobiology of dendritic cells. *Ann Rev Immunol* 2000; 18:767-811.

Basu S, Binder R J, Suto R, Anderson K M, Srivastava P K. Necrotic but not apoptotic cell death releases heat shock proteins, which deliver a partial maturation signal to dendritic cells and activete the NFkappaB pathway. *Int Immunol* 2000; 12:1539-46.

Bendz H, Ruhland S C, Pandya M J, Hainzl O, Riegelsberger S, Braüchle C, Mayer M P, Buchner J, Issels R D, Noessner E. Human heat shock protein 70 enhances tumor antigen presentation through complex formation and intracellular antigen delivery without innate immune signaling. *J Biol Chem* 2007; 282(43):31688-702.

Bhowmick S J, Bischof J C. Supraphysiological thermal injury in Dunning AT-1 prostate tumor cells. In: *Adv Heat Mass Transf Biotechnol* 1998; 40:77-78.

Bogdanovich UIa. [Use of lasers for the treatment of injuries and diseases of the musculoskeletal system]. *Sov Med* 1980; (3):61-6.

Bomford R. Will adjuvants be needed for vaccines of the future? In: Brown F, Haaheim L R, (eds). *Modulation of the Immune Response to Vaccine Antigens*. Developing Biological Standards, Vol. 92. Basel:Karger, 1998:13-8.

Capon A, Mordon C. Can thermal lasers promote skin wound healing? *Am J Clin Dermatol* 2003; 4(1):1-12.

Canti G, Lattuada D, Nicolin A, Taroni P, Valentini G, Cubeddu R. Antitumor immunity induced by photodynamic therapy with aluminum disulfonated phthalocyanines and laser light. *Anti-Cancer Drugs* 1994; 5(4):443-7.

Carter D. Dose-sparing formulations and adjuvants for intradermal injection. Presentation to the Emergency Vaccine Technologies for Epidemics and Disasters: Manufacture, Delivery and Administration Workshop. Dulles, V A, Nov. 29-30, 2007.

Chen W R, Adams R L, Carubelli R, Nordquist R E. Laser photosensitizer-assisted immunotherapy: a novel modality For cancer treatment. *Cancer Lett* 1997; 115(1):25-30.

Chen W R, Huang Z, Korbelik M, Nordquist R E, Liu H. Photoimmunotherapy for cancer treatment. *J Environ Pathol Toxicol Oncol* 2006; 25(1-2):281-91.

Couch R B. Nasal vaccination, *Escherichia coli* enterotoxin, and Bell's palsy. *N Engl J Med* 2004; 350:860-1.

Desmettre T, Maurage C A, Mordon S. Heat shock protein hyperexpression on chorioretinal layers after transpupillary thermotherapy. *Inves Ophthalmol Visual Sci* 2001; 42(12):2976-2980.

Dieu M C, Vanbervliet B, Vicari A, Bridon J M, Oldham E, Ait-Yahia S, Briere F, Zlotnik A, Lebecque S, Caux C. Selective recruitment of immature and mature dendritic cells by distinct chemokines expressed in different anatomic sites. *J Exp Med* 1998; 188(2):373-86.

Diller K R, Pearce J A. Issues in modeling thermal alterations in tissues. *Ann NY Acad Sci* 1999; 888:153-164.

Emohare O; Hafez M I; Sandison A; Coombs R R H; McCarthy I D. Laser-induced thermal stress and the heat shock response in neural cells. *Acta Orthoped* 2004; 75(5):610-617.

Ferrando R E, Schuschereba S T, Bowman P D, Quong J A, Yang J M, Stuck B E. Heat shock protein induction in human cells by CO2 laser irradiation. Defense Technical Information Center Report ADA266430, Jun. 14, 1993.

Fitzhugh D J, Naik S, Gonzalez E, Caughman S W, Hwang S T. CC chemokine receptor 6 (CCR6) is a marker for memory T cells that arrest on activated human dermal microvascular endothelium under shear stress. *J Invest Dermatol* 2000; 115(2):332.

Flotte T J, Anderson T, McAuliffe D J, Hasan T, Doukas A G. Laser-induced enhancement of cytotoxicity: A new approach to cancer therapy. In: Jacques S L, ed. *Laser-Tissue Interactions IV*. Proc SPIE 1993; 1882:122-129.

Flotte T J, Lee S, Zhang H, McAuliffe D J, Douki T, Doukas A G. Laser-induced stress waves: Applications for molecular delivery. In: Jacques S L, ed. *Laser-Tissue Interactions VI*. Proc SPIE 1995; 2391:202-207.

Fushimi T, Kojima A, Moore M A, Crystal R G. Macrophage inflammatory protein 3alpha transgene attracts dendritic cells to established murine tumors and suppresses tumor growth. *J Clin Invest* 2000; 105(10):1383-93.

Fushimi T, O'Connor T P, Crystal R G. Adenoviral gene transfer of stromal cell-derived factor-1 to murine tumors induces the accumulation of dendritic cells and suppresses tumor growth. *Cancer Res* 2006; 66(7):3513-22.

Glenney A T, Pope C G, Waddington H, Wallace U. XXIII—The antigenic value of toxoid precipitated by potassium alum. *J Pathol Bacteriol* 1926; 29:38-9.

Gollnick S O, Owczarczak B, Maier P. Photodynamic therapy and anti-tumor immunity. *Laser Surg Med* 2006; 38:509-515.

Green D M, Diller K R. Measurement of burn induced leakage of macromolecules in living tissue. *Trans. ASME J Biomech Eng* 1978; 100:153-158.

Gupta R K, Rost B E, Relyveld E, Siber G R, Adjuvant properties of aluminum and calcium compounds. In: Powell M F, Newman M J (eds). *Vaccine Design: the Subunit and Adjuvant Approach*. New York: Plenum Press, 1995:229-48.

Hatzfeld-Charbonnier A S, Lasek A, Castera L, Gosset P, Velu T, Formstecher P, Mortier L, Marchetti P. Influence of heat stress on human monocyte-derived dendritic cell functions with immunotherapeutic potential for antitumor vaccines. *J Leukoc Biol* 2007; 81(5):1179-87.

Henderick J P, Hartl F U. Molecular chaperone functions of heat shock proteins. *Ann Rev Biochem* 1993; 62:349-84.

HogenEsch H. Mechanisms of stimulation of the immune response by aluminum adjuvants. *Vaccine* 2002; 20(Suppl 3):S34-S39.

Ivarsson K, Myllymäki L, Jansner K, Stenram U, Tranberg K G. Resistance to tumour challenge after tumour laser thermotherapy is associated with a cellular immune response. *Br J Cancer* 2005; 93(4):435-40.

Khromov B M. [Laser therapy of diseases and injuries (review of the literature)] Vrach Delo 1978; 10:115-9. Russian Korbelik M, Sun J, Cecic I. Photodynamic therapy-induced cell surface expression and release of heat shock proteins: relevance for tumor response. *Cancer Res* 2005; 65(3): 1018-26.

Law M. The Induction of thermal resistance in the ear of the mouse by heating at temperatures ranging from 41.5 to 45.5° C. *Rad Res* 1981; 85(1):126-134.

Li G C, Werb Z. Correlation between synthesis of heat shock proteins and development of thermotolerance in Chinese hamster fibroblasts. *Proc Natl Acad Sci USA* 1982; 79:3218-3222.

Lucas C, Criens-Poublon L J, Cockrell C T, de Haan R J. Wound healing in cell studies and animal model experiments by low level laser therapy; were clinical studies justified? A systematic review. *Lasers Med Sci* 2002; 17(2):110-34.

Mambula S S, Calderwood S K. Heat shock protein 70 is secreted from tumor cells by a nonclassical pathway involving lysosomal endosomes. *J Immunol* 2006; 177 (11):7849-57.

McAuliffe D J, Lee S, Flotte T J, Doukas A G. Stress wave-assisted transport through the plasma membrane in vitro. *Lasers Surg Med* 1997; 20:216-222.

Mester E, Lu'dfrny G, Vajda 'G, Tota J: Uber die wirkung von laser-strahlen auf die bakteriumphagocytose der leukocyten. *Acta Biol Med German* 1968; 21: 317.

Mester E, Spiry T, Szende B, Tota J G. Effect of laser rays on wound healing. *Am J Surg* 1971; 122(4):532-5.

Mester E, Nagylucskay S, Tisza S, Mester A. Stimulation of wound healing by means of laser rays. Part III—Investigation of the effect on immune competent cells. *Acta Chir Acad Sci Hung* 1978; 19(2):163-70.

Minowada G, Welch W J. Clinical implications of the stress response. *J Clin Invest* 1995; 95:3-12.

Miyamoto Y, Umebayashi Y, Koyano M, Wakita M, Nishisaka T. Enhancement of cytotoxic effect of bleomycin with transient permeabilization of plasma membrane by laser-induced multiple stress waves in vitro. *Cancer Lett* 2003; 199(1):45-51.

Moritz A, Henriques F. Studies of thermal injury II: the relative importance of time and surface temperature in the caucasian of cutaneous burns. Am J Pathol 1947; 23: 695-720.

Mulholland S E, Lee S, McAuliffe D J, Doukas A G. Cell loading with laser-generated stress waves: the role of stress gradients. *Pharm Res* 1999; 16(4):514-518.

Nagel J, Svec D, Water T, Fireman P. IgE synthesis in man. Part I. Development of specific IgE antibodies after immunization with tetanus-diphtheria (TD) toxoids. *J Immunol* 1977; 118:334-41.

Novoselova E G, Glushkova O V, Cherenkov D A, Chudnovsky V M, Fesenko E E. Effects of low-power laser radiation on mice immunity. *Photodermatol Photoimmunol Photomed* 2006a; 22(1):33-8.

Núñez S C, Nogueira G E C, Ribeiro M S, Garcez A S, Lage-Marques J L. He—Ne laser effects on blood microcirculation during wound healing: a method of in vivo study through laser Doppler flowmetry. *Lasers Surg Med* 2004; 35:363-368.

Onikienko S B, Zemlyanoy A B, Margulis B A, Guzhova I V, Varlashova M B, Gornostaev V S, Tikhonova N V, Baranov G A, Lesnichiy V V. [Diagnostics and correction of the metabolic and immune disorders. Interactions of bacterial endotoxins and lipophilic xenobiotics with receptors associated with innate immunity]. *Donosologiya* (St. Petersburg) 2007; 1:32-54. Russian language.

Ostberg J R, Patel R, Repasky E A. Regulation of immune activity by mild (fever-range) whole body hyperthermia: effects on epidermal Langerhans cells. *Cell Stress Chaperones* 2000; 5:458-461.

Posten W, Wrone D A, Dover J S, Arndt K A, Silapunt S, Alam M. Low-level laser therapy for wound healing: mechanism and efficacy. *Dermatol Surg* 2005; 31(3):334-40.

Reinisch L. Scatter-limited phototherapy: a model for laser treatment of skin. *Lasers Surg Med* 2002; 30(5):381-8.

Ribeiro M S, Silva D F T, Maldonado E P, de Rossi W, Zezell D M. Effects of 1047-nm neodymium laser radiation on skin wound healing. J Clin Laser Surg Med 2002; 20:37-40.

Roggan A, Miller G. Dosimetry and computer-based irradiation planning for laser-induced interstitial thermotherapy (LITT). In: Laser-Induced Interstitial Thermotherapy. Roggan A, Miller G (eds.) Society of Photo-Optical Instrumentation Enginering, 1995:114-156.

Saperia D, Gassberg E, Lyons R F, Abergel R P, Baneux P, Castel J C, Dwyer R M, Uitto J. Demonstration of elevated type I and type III procollagen mRNA levels in cutaneous wounds treated with helium-neon laser. *Biochem Biophys Res Commun* 1986; 138:1123-1128.

Schindl A, Merwald H, Schindl L, Kaun C, Wojta J. Direct stimulatory effect of low-intensity 670 nm laser irradiation on human endothelial cell proliferation, *Br J Dermatol* 2003; 148:334-336.

Sliney D, Wolbarsht M. *Optical Radiation Hazards to the Skin, in Safety with Lasers and other Optical Sources.* New York: Plenum Press, 1980:161-85.

Souil E, Capon A, Mordon S, Dinh-Xuan A T, Polla B S, Bachelet M. Treatment with 815-nm diode laser induces long-lasting expression of 72-kDa heat shock protein in normal rat skin. *Br J Dermatol* 2001; 144(2):260-6.

Sozzani S, Sallusto F, Luni W, Zhou D, Piemonti L, Allavena P, Van Damme J, Valitutti S, Lanzavecchia A, Mantovani A. Migration of dendritic cells in response to formyl peptides, C5a and a distinct set of chemokines. *J Immunol* 1995; 155:3292-3295.

Tang W, Weidner D A, Hu B Y, Newton R J, Hu X H. Efficient delivery of small interfering RNA to plant cells by a nanosecond pulsed laser-induced stress wave for posttranscriptional gene silencing. Plant Sci 2006; 171(3):375-381.

Terakawa M, Ogura M, Sato S, Wakisaka H, Ashida H, Uenoyama M, Masaki Y, Obara M. Gene transfer into mammalian cells by use of a nanosecond pulsed laser-induced stress wave. *Opt Lett* 2004; 29(11):1227-9.

U.S. Food and Drug Administration. Summary Minutes—Allergenic Products Advisory Committee and Report on Safety Considerations for the Aluminum Component of Alum-precipitated Allergenic Extracts, Office of Biologics Research and Review, Biologics Information Staff. Bethesda: FDA, 1987 (NFN-20).

U.S. Department of Health and Human Services. *Accelerated Development of Vaccines* 2002. The Jordan Report. Washington D.C.:US Health and Human Services, 2002.

Venugopalan V, Nishioka N S, Miki B B. Thermodynamic response of soft biological tissues to pulsed infrared-laser irradiation. *Biophys Jnl* 1996; 70:2981-2993.

Vogel A, Venugopalan V. Mechanisms of pulsed laser ablation of biological tissues. *Chem Rev* 2003; 103:577-644.

Welch A J. The thermal response of laser irradiated tissue. *IEEE Jnl Quantum Electron* 1984; QE-20(12): 1471-1481.

Xu L L, Warren M K, Rose W L, Gong W H, Wang J M. Human recombinant monocyte chemotactic protein and other C—C chemokines bind and induce directional migration of dendritic cells in vitro. *J Leukocyte Biol* 1996; 60:365-371.

Zanardi L R, Haber P, Mootrey G T, Niu M T, Wharton M. Intussusception among recipients of rotavirus vaccine: reports to the Vaccine Adverse Event Reporting System. *Pediatrics* 2001; 107(6):e97.

Zhang X, Yu C, Zhao J, Fu L, Yi S, Liu S, Yu T, Chen W. Vaccination with a DNA vaccine based on human PSCA and HSP70 adjuvant enhances the antigen-specific CD8+ T-cell response and inhibits the PSCA+ tumors growth in mice. *J Gene Med* 2007; 9(8):715-26.

All references, patents, patent applications, and GenBank numbers are each incorporated herein by reference by this statement as if each were incorporated by reference individually.

What is claimed is:

1. A method of generating an enhanced immune response in a subject comprising administering a vaccine composition to a subject via intradermal, subcutaneous, and intramuscular injection in combination with non-destructive laser radiation, wherein the laser radiation is administered to the subject within an hour of the vaccine administration to the subject, thereby generating an enhanced immune response from a subject, as compared to an immune response without the use of laser radiation, wherein the vaccine composition further comprises HSP 70.

2. The method of claim 1, wherein the enhanced immune response is generated from a non-responsive subject.

3. The method of claim 1, to generate the enhanced immune response from the subject with an increased HSP 70 concentration.

4. The method of claim 1, wherein the non-destructive laser radiation has of a frequency of the laser is about 1 to about 20 kilohertz, a power of the laser is about 1 to about 10 watts, and a pulse duration is about 1 to about 1000 nanoseconds.

5. The method of claim 1, wherein the previous exposure to the non-destructive laser radiation was of a wavelength of 510 nm and 578 nm.

6. The method of claim 1, wherein the previous exposure to the non-destructive laser radiation was from a neodymium-doped yttrium aluminum garnet (Nd:YAG) laser.

7. The method of claim 1, wherein the enhanced immune response comprises an increase in an antibody titer specific to the vaccine.

8. The method of claim 1, wherein the enhanced immune response comprises an increased resistance to a condition characterized by a decrease in infection rate upon exposure to a pathogen specific to the vaccine, a decrease in mortality in response to exposure to a pathogen specific to the vaccine, or a decrease in time to detect a response to the vaccine.

9. The method of claim 1, wherein the laser radiation is administered either before or after administration of the vaccine to the subject.

* * * * *